US012679863B2

(12) United States Patent
Snovida et al.

(10) Patent No.: US 12,679,863 B2
(45) Date of Patent: Jul. 14, 2026

(54) PEPTIDE PURIFICATION FORMULATIONS AND METHODS

(71) Applicant: PIERCE BIOTECHNOLOGY, INC., Rockford, IL (US)

(72) Inventors: Sergei Snovida, Rockford, IL (US); Ryan Bomgarden, Winnebago, IL (US); Amarjeet Flora, Woodstock, IL (US)

(73) Assignee: Life Technologies Corporation, Carlsbad, CA (US)

( * ) Notice: Subject to any disclaimer, the term of this patent is extended or adjusted under 35 U.S.C. 154(b) by 749 days.

(21) Appl. No.: 17/764,354

(22) PCT Filed: Oct. 13, 2020

(86) PCT No.: PCT/US2020/055368
§ 371 (c)(1),
(2) Date: Mar. 28, 2022

(87) PCT Pub. No.: WO2021/076489
PCT Pub. Date: Apr. 22, 2021

(65) Prior Publication Data
US 2022/0396598 A1    Dec. 15, 2022

Related U.S. Application Data

(60) Provisional application No. 62/914,796, filed on Oct. 14, 2019.

(51) Int. Cl.
*C07K 1/18* (2006.01)
*G01N 1/34* (2006.01)
*G01N 30/06* (2006.01)
*G01N 33/68* (2006.01)

(52) U.S. Cl.
CPC ................ *C07K 1/18* (2013.01); *G01N 1/34* (2013.01); *G01N 33/6848* (2013.01); *G01N 2030/062* (2013.01)

(58) Field of Classification Search
CPC ........ C07K 1/18; G01N 1/34; G01N 33/6848; G01N 2030/062
See application file for complete search history.

(56) References Cited

U.S. PATENT DOCUMENTS

| | | |
|---|---|---|
| 2004/0009567 A1 | 1/2004 | Duewel et al. |
| 2009/0148435 A1 | 6/2009 | Lebreton et al. |
| 2012/0231537 A1 | 9/2012 | Templeton et al. |
| 2013/0011925 A1 | 1/2013 | Gilar et al. |
| 2013/0079272 A1 | 3/2013 | Liu et al. |
| 2013/0309689 A1 | 11/2013 | Rogers et al. |
| 2015/0087073 A1 | 3/2015 | Chambers et al. |
| 2018/0078876 A1 | 3/2018 | Wang et al. |
| 2018/0201644 A1 | 7/2018 | Kulak et al. |

FOREIGN PATENT DOCUMENTS

| | | |
|---|---|---|
| CN | 1176659 A | 3/1998 |
| CN | 101333244 A | 12/2008 |
| CN | 102239175 A | 11/2011 |
| CN | 103687790 A | 3/2014 |
| CN | 107849085 A | 3/2018 |
| EP | 3115369 A1 | 1/2017 |
| JP | 2011502161 A | 1/2011 |
| JP | 2011519560 A | 7/2011 |
| JP | 2013530156 A | 7/2013 |
| WO | WO-2008148645 A1 | 12/2008 |
| WO | WO-2009058812 A1 | 5/2009 |
| WO | WO-2012058619 A1 | 5/2012 |
| WO | WO-2014066471 A1 | 5/2014 |
| WO | WO-2015059478 A1 | 4/2015 |
| WO | WO-2016149088 A1 | 9/2016 |
| WO | WO-2017005898 A1 | 1/2017 |

OTHER PUBLICATIONS

Kalocsay. "APEX Peroxidase-Catalyzed Proximity Labelling and Multiplexed Quantitative Proteomics." Proximity Labeling Methods and Protocols. Eds. Sunbul and Jaschke, Humana Press. (Year: 2008).*
Kulak N.A., et al., "Minimal, Encapsulated Proteomic-Sample Processing Applied to Copy-Number Estimation in Eukaryotic Cells, " Nature Methods, Mar. 2014, vol. 11, No. 3, pp. 319-324.
Zhao Z., et al., "A Novel Method of Preparation Samples for Mass Spectrometry Analysis of Histones," China Academic Journal, Oct. 15, 2013, vol. 23, No. 5, pp. 59-63.
Adiga R et al., "Point-of-care production of therapeutic proteins of good-manufacturing-practice quality", Nature Biomedical Engineering, Nature Publishing Group UK, London, vol. 2, No. 9, Jul. 9, 2018 (Jul. 9, 2018), pp. 675-686, XP036587247, DOI: 10.1038/S41551-018-0259-1 [retrieved on Jul. 9, 2018].
Agilent Technologies: "Agilent Bond Elut Plexa and Polymeric SPE Selection Guide," The Measure of Confidence, 2011, 24 pages.
Agilent Technologies: "Agilent's New Mixed-Mode Cation Exchange Polymer Solid-Phase Extraction Cartridges: SampliQ SCX," Agilent Technologies—Technical Note, 2008, 4 pages.
Balcke G.U., et al., "An UPLC-MS/MS Method for Highly Sensitive High-Throughput Analysis of Phytohormones in Plant Tissues," Plant Methods, 2012, vol. 8, No. 47, 11 pages.
Borner G H, et al., "Using In-Solution Digestion, Peptide Fractionation, and a Q Exactive Mass Spectrometer to Analyze the Proteome of Clathrin-Coated Vesicles," Cold Spring Harbor Protocols, Nov. 2014, vol. 11, pp. 1192-1195.
Chambers E.E., "Improving the Sensitivity and Specificity of LC/MS to Enable Bioanalysis of Therapeutic and Endogenous Proteins and Peptides," Analytical and Environmental Sciences Research Division School of Biomedical Sciences, 2014, 372 pages.
(Continued)

*Primary Examiner* — Suzanne M Noakes
*Assistant Examiner* — Ciara A Mcknight
(74) *Attorney, Agent, or Firm* — Priya D. Subramony

(57) ABSTRACT

Improved formulations for purification of peptide from biological samples and methods and kits for purifying peptides from biological samples (e.g., cells and tissues), as well as use of purified peptides (e.g., polypeptides derived from protein digests) in mass spectrometry (e.g., LC-MS) applications are described.

18 Claims, 12 Drawing Sheets

(56) References Cited

OTHER PUBLICATIONS

Danaceau J.P., et al., "Removal of Pharmaceutical Dosing Excipients from Plasma Samples using Mixed-Mode Solid Phase Extraction (SPE)," Waters the Science of What's Possible, 2012, 1 page.

Gad S.C., "Preclinical Development Handbook," ADME and Biopharmaceutical Properties, Wiley, 2008, 1347 pages.

Hui Y., "Development, Validation and Application of Analytical Methods to Measure Prognostic Biomarkers in Patients Receiving on-Pump Coronary Artery Bypass Grafting Surgery," The University of British Columbia, 2013, 204 pages.

Jenkins K.M., et al., "Mixed-Mode Solid-Phase Extraction Procedures for the Determination of MDMA and Metabolites in Urine Using LC-MS, LC-UV, or GC-NPD," Journal of Analytical Toxicology, 2004, vol. 28, pp. 50-58.

Mazanek M., et al., "A New Acid Mix Enhances Phosphopeptide Enrichment on Titanium-and Zirconium Dioxide for Mapping of Phosphorylation Sites on Protein Complexes," Journal of Chromatography, 2010, pp. 515-524.

PCT/US2020/055368, International Search Report and Written Opinion, Feb. 5, 2021, 14 pages.

Waters: "Chromatography Columns and Supplies Catalog," The Science of what's Possible, 2008, 289 pages.

Waters: "ProteinWorks µElution SPE Clean-up Kit," Waters MCX flyer, Care and Use Manual, Jan. 2016, 8 pages.

Wiederin J.L., et al., "Plasma Proteomic Analysis of Simian Immunodeficiency Virus Infection of Rhesus Macaques," Journal of Proteome Research, Sep. 3, 2010, 9(9), pp. 4721-4731.

Williams L., et al., "The Use of Mixed-Mode SPE to Minimize LC-MS Matrix Effects Due to Dosing Vehicles," Biotage, 2006, 6 pages.

Yuan L, et al., "Systematic investigation of orthogonal SPE sample preparation for the LC-MS/MS bioanalysis of a monoclonal antibody after pellet digestion.", Bioanalysis, 2013, vol. 5, No. 19, pp. 2379-2391.

* cited by examiner

PEPTIDE PURIFICATION FORMULATIONS AND METHODS

CROSS-REFERENCE TO RELATED APPLICATIONS

This application is a U.S. National Application filed under 35 U.S.C. § 371 of International Application No. PCT/US2020/055368, filed Oct. 13, 2020, which claims the benefit of priority under 35 U.S.C. § 119 to U.S. Provisional Application No. 62/914,796, filed Oct. 14, 2019, which disclosures are herein incorporated by reference in their entirety.

TECHNICAL FIELD

Formulations for purification of peptides from biological samples and methods and kits for purifying peptides (e.g., polypeptides derived from protein digests) from biological samples, as well as use of purified peptides in downstream applications such as mass spectrometry are described.

BACKGROUND

Mass spectrometry (MS) is a powerful tool for analyzing proteins and their amino acid sequences, including post-translational modifications. A typical method for preparing a protein sample for MS analysis is to first digest the protein with enzymes (e.g., trypsin, Lys-C, and the like) to produce a mixture of smaller peptide fragments and subsequently analyze the fragments on an LC-MS system to extract qualitative and/or quantitative proteomic information (referred to herein as a "bottom-up" proteomics workflow). In a typical "bottom-up" proteomics workflow, proteins generally need to be extracted from a biological sample prior to digestion. A biological sample (e.g., tissues, cultured cells, and biological fluids) is a complex matrix containing various small molecules, carbohydrates, lipids, nucleic acids, salts, peptides and proteins. Many of these components are native to the biological samples and some are added during sample preparation to improve solubility of proteins, introduce desired chemical modifications to proteins/peptides, or maintain optimal pH for proteolytic activity during protein digestion. It is important to remove as many of the non-peptide species from the sample matrix as possible prior to LC-MS analysis to prevent chromatographic interference, ionization suppression, and clogging of the LC plumbing components. This clean-up step is commonly known as "sample desalting". Conventionally, this procedure is performed on a reversed-phase resin using solid phase extraction (SPE) chromatography, where a sample first is acidified and then loaded onto the resin in an aqueous solution. Once the sample is loaded onto the resin, the resin is washed with an aqueous solution to remove small hydrophilic molecules and ions. Peptides remain bound to the resin by hydrophobic interactions and are eluted with an acidic solution containing organic solvent (e.g., 50% acetonitrile in water). A drawback of this desalting method is that hydrophobic molecules, such as lipids and detergents, also bind to the resin and co-elute with the peptide sample. As a result, the peptide sample is contaminated with the hydrophobic molecules that can lead to poor quality data and damage to the LC equipment. Thus, there is a need for improved formulations, alternative stationary phases, and desalting solution formulations and methods for purifying proteins and peptides from biological samples, whereby the proteins and peptides are sufficiently pure for high quality analysis by LC-MS.

SUMMARY

In one aspect, methods and kits are disclosed herein for use in purifying a sample that includes a peptide. Samples include those of biological origin, those prepared synthetically and combinations thereof. In some embodiments, the peptide includes 2-50 amino acid residues. In some embodiments, the sample includes two or more peptides. In some embodiments, the sample is a digested protein or polypeptide. The sample can further include a salt, detergent, a lipid, a small neutral molecule, or a combination thereof. The sample can further include one or more contaminants. The contaminant can be a hydrophilic contaminant such as a neutral contaminant, an anionic contaminant, or a combination thereof. In some embodiments, the sample includes a hydrophobic contaminant such as a lipid or a detergent. In some embodiments, hydrophilic contaminant is a salt, nucleic acid, or a carbohydrate. In some embodiments, the sample includes a monovalent cationic contaminant such as ammonium, sodium, potassium, tris(hydroxymethyl)aminomethane (tris), hydroxylamine, ethanolamine, HEPES (4-(2-hydroxyethyl)-1-piperazineethanesulfonic acid), PIPES (piperazine-N,N'-bis(2-ethanesulfonic acid)), EPPS (4-(2-hydroxyethyl)-1-piperazinepropanesulfonic acid), glycine, a mass tag, or a combination thereof. In some embodiments, the monovalent cationic contaminant is or includes a mass tag or derivative thereof.

In another aspect, a method of purifying a sample (e.g., a biological sample) is provided that includes:

(a) contacting the biological sample with a hydrophobic, polymer-based cation exchange material under acidic conditions, such that the sample binds to the cation exchange material, wherein the sample includes: (i) a peptide, and (ii) a monovalent cationic contaminant and/or a hydrophobic contaminant;

(b) washing the cation exchange material with an acidic solution, wherein the acidic solution includes greater than 20% (v/v) volatile organic solvent, water, and a volatile salt, such that the peptide is retained on the cation exchange material and the monovalent cationic and/or hydrophobic contaminant is removed from the cation exchange material; and (c) eluting the retained peptide from the cation exchange material with an alkaline or neutral solution, wherein the alkaline or neutral solution includes a volatile organic solvent, water, and a volatile compound selected from a volatile base, a volatile salt and a combination thereof.

In yet another aspect, a method of purifying a sample (e.g., biological sample) is provided that includes:

(a) contacting the biological sample with a hydrophobic, polymer-based cation exchange material under acidic conditions, such that the sample binds to the cation exchange material, wherein the sample includes: (i) a peptide, (ii) a monovalent cationic contaminant and/or a hydrophobic contaminant, and (iii) a hydrophilic contaminant;

(b) washing the cation exchange material with a first acidic solution, wherein the first acidic solution includes greater than 20% (v/v) volatile organic solvent, water, and a volatile salt, such that the peptide is retained on the cation exchange material and the monovalent cationic and/or hydrophobic contaminant is removed from the cation exchange material;

(c) washing the cation exchange material with a second acidic solution, wherein the second acidic solution includes 20% or less (v/v) volatile organic solvent, water, and a volatile acid, wherein the peptide is retained on the cation exchange material and the hydrophilic contaminant is removed; and (d) eluting the retained peptide from the cation exchange material with an alkaline or neutral solution, wherein the alkaline or neutral solution includes a volatile organic solvent, water, and a volatile compound selected from a volatile base, a volatile salt and a combination thereof.

In yet another aspect, a method of purifying a sample (e.g., a biological sample) is provided that includes:

(a) contacting the biological sample with a hydrophobic, polymer-based cation exchange material under acidic conditions, such that the sample binds to the cation exchange material, wherein the biological sample includes: (i) a peptide, (ii) a monovalent cationic contaminant and/or a hydrophobic contaminant, and (iii) a hydrophilic contaminant;

(b) washing the cation exchange material with a first acidic solution, wherein the first acidic solution includes 20% or less (v/v) volatile organic solvent, water, and a volatile acid, such that peptide is retained on the cation exchange material and the hydrophilic contaminant is removed from the cation exchange material;

(c) washing the cation exchange material with a second acidic solution, wherein the second acidic solution includes greater than 20% (v/v) volatile organic solvent, water and a volatile salt, wherein the peptide is retained on the cation exchange material and the monovalent cationic and/or hydrophobic contaminant is removed from the cation exchange material; and (d) eluting the retained peptide from the cation exchange material with an alkaline or neutral solution, wherein the alkaline or neutral solution includes a volatile organic solvent, water, and a volatile compound selected from a volatile base, a volatile salt, and a combination thereof.

In any of the methods disclosed herein, the sample can be contacted with the hydrophobic, polymer-based cation exchange material at a pH 1-5; the cation exchange material can be washed at a pH 1-5; and/or the sample can be eluted from the cation exchange material at greater than pH 5 (e.g., 5-11). In certain methods, the retained peptide can be eluted from the cation exchange material with an alkaline or neutral solution, wherein the alkaline or neutral solution includes a volatile organic solvent, water, and a volatile salt. In certain embodiments, methods disclosed herein can further include treating the biological sample with a proteolytic enzyme (e.g., trypsin or Lys-C) to produce the peptide prior to contacting the biological sample with the cation exchange material.

In yet another aspect, a kit for purifying a biological sample that includes a peptide is provided. The kit can include: (a) a hydrophobic, polymer-based cation exchange material; (b) an acidic solution including a volatile salt, water and greater than 20% (v/v) volatile organic solvent; (c) a neutral or alkaline solution including a volatile base, water and a volatile organic solvent; and (d) instructions for using the kit to purify the biological sample.

In yet another aspect, a kit for purifying a biological sample that includes a peptide is provided. The kit can include: (a) a hydrophobic, polymer-based cation exchange material; (b) an acidic solution including greater than 20%

(v/v) volatile organic solvent, a volatile salt, and water, (c) an acidic solution including 20% or less (v/v) volatile organic solvent, a volatile salt, and water; (d) a neutral or alkaline solution including a volatile base, water, and a volatile organic solvent; and (e) instructions for using the kit to purify the biological sample.

In any of the methods and kits provided herein, the hydrophobic, polymer-based cation exchange material can be a sulfonated divinyl benzene polystyrene, sulfonated polydivinyl benzene, or sulfonated divinyl benzene/polystyrene/pyrrolidone resin. In some embodiments, the volatile salt can include a volatile acid and a volatile base. For example, the volatile acid can be formic acid, acetic acid, trifluoracetic acid, or trichloroacetic acid. Representative examples of a volatile base include trimethylamine, ammonia, triethylamine, piperidine, and butylamine. In any of the methods and kits provided herein, the volatile organic solvent can be acetonitrile, methanol, ethanol, n-propanol, iso-propanol, acetone, or a combination thereof.

DETAILED DESCRIPTION

Figure 1:
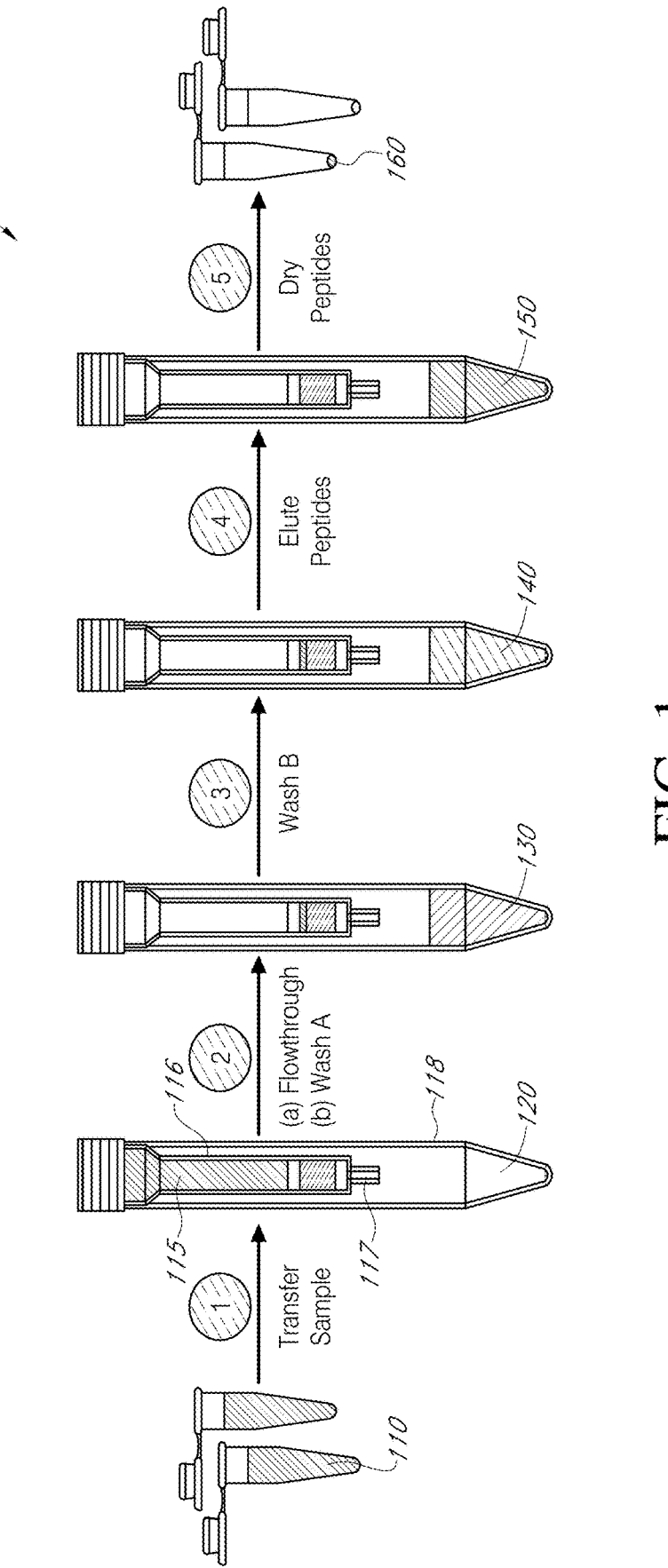
FIG. 1 is a schematic of a peptide purification method using multiple wash solutions.
Figure 2A:
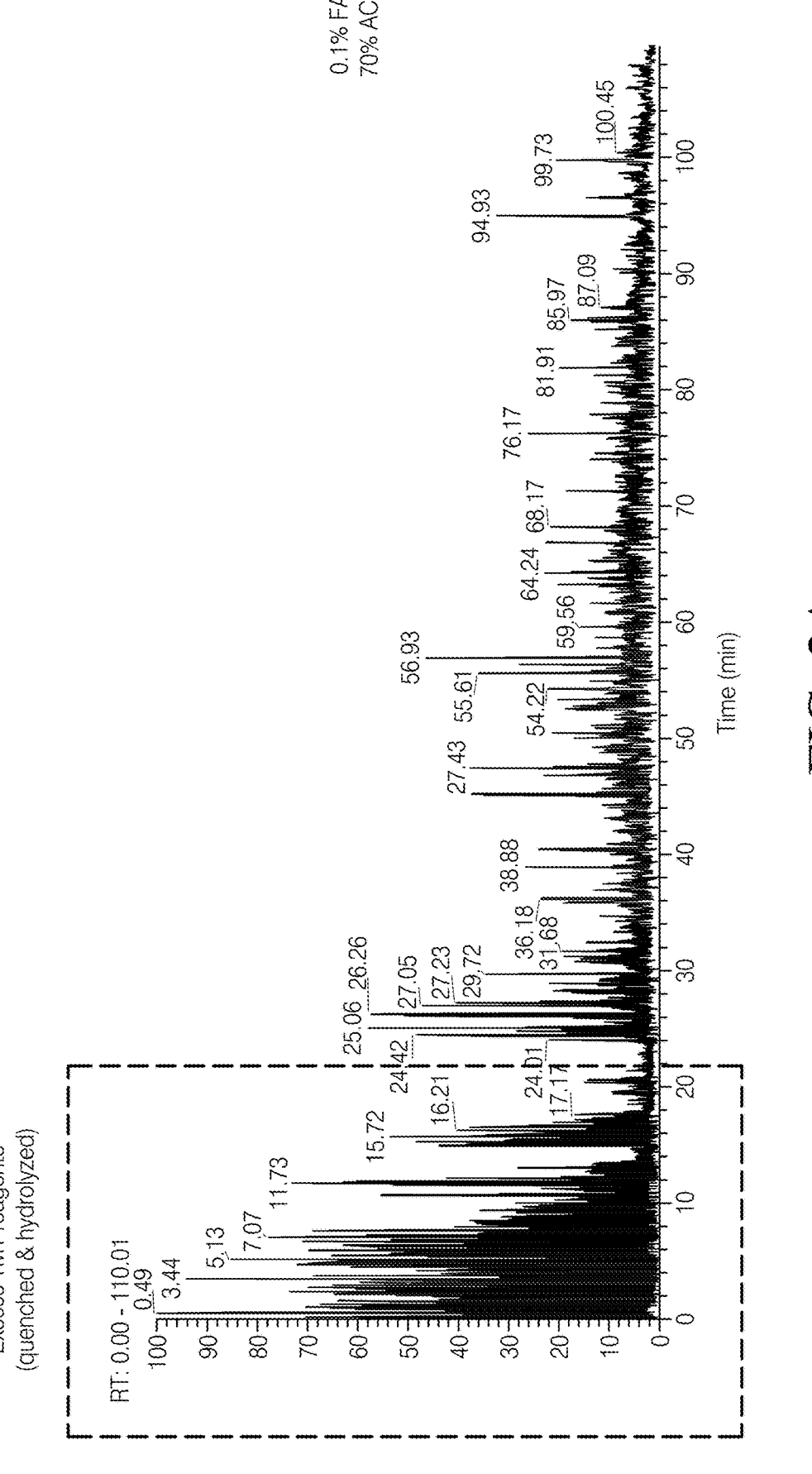
FIG. 2 shows MS (total ion) chromatograms of HeLa cell protein digests labeled with TMT reagent and cleaned-up with the Wash B solution containing 0.1% formic acid (FIG. 2A), Wash B solution containing 0.1% (v/v) formic acid and 0.1% (v/v) triethylamine (FIG. 2B), and Wash B solution containing 0.5% (v/v) formic acid and 0.5% (v/v) triethylamine (FIG. 2C). Boxed region of the chromatograms shows the signal due to TMT-derived ions (quenched and hydrolyzed).
Figure 2B:
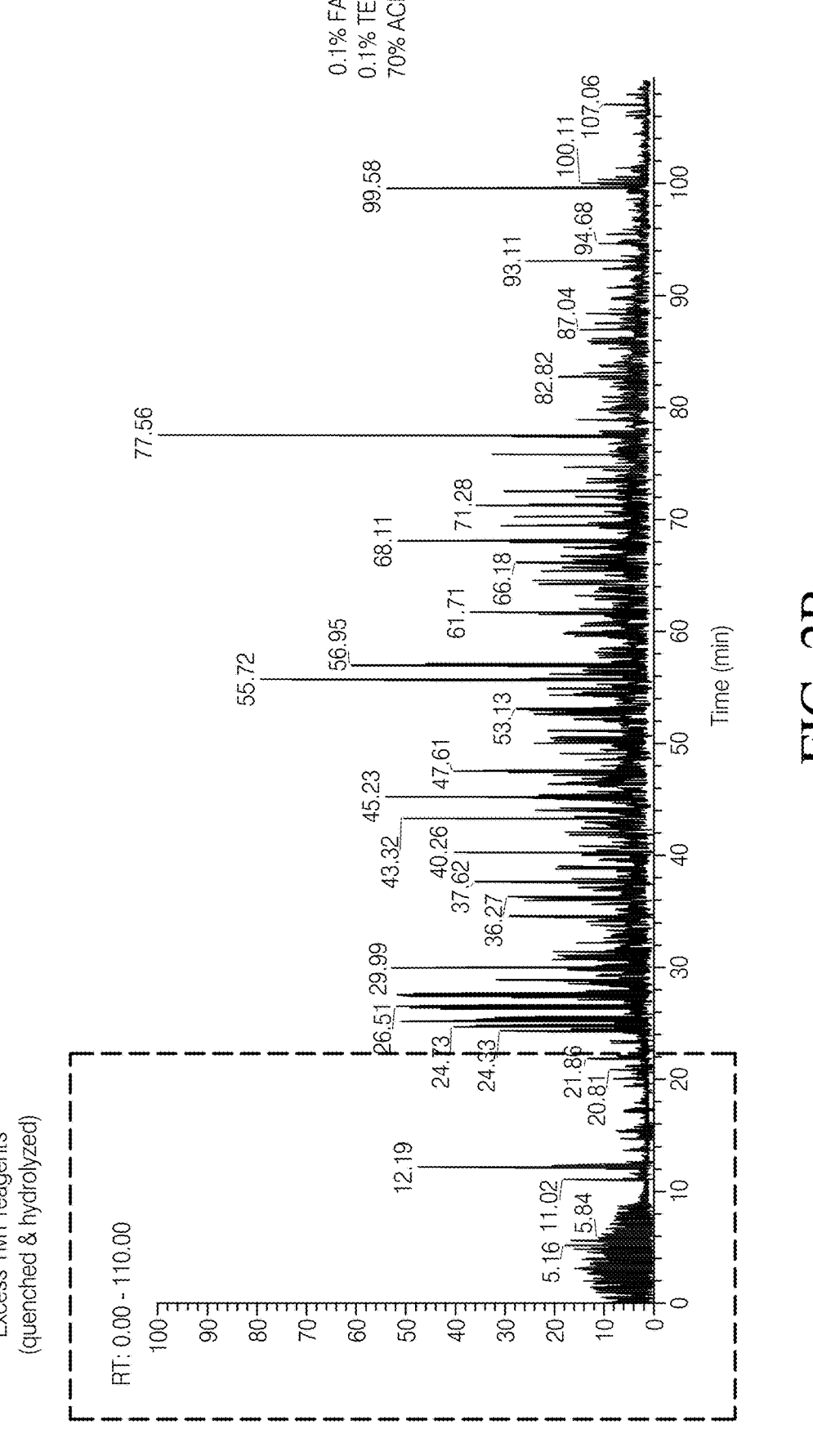
Figure 2C:
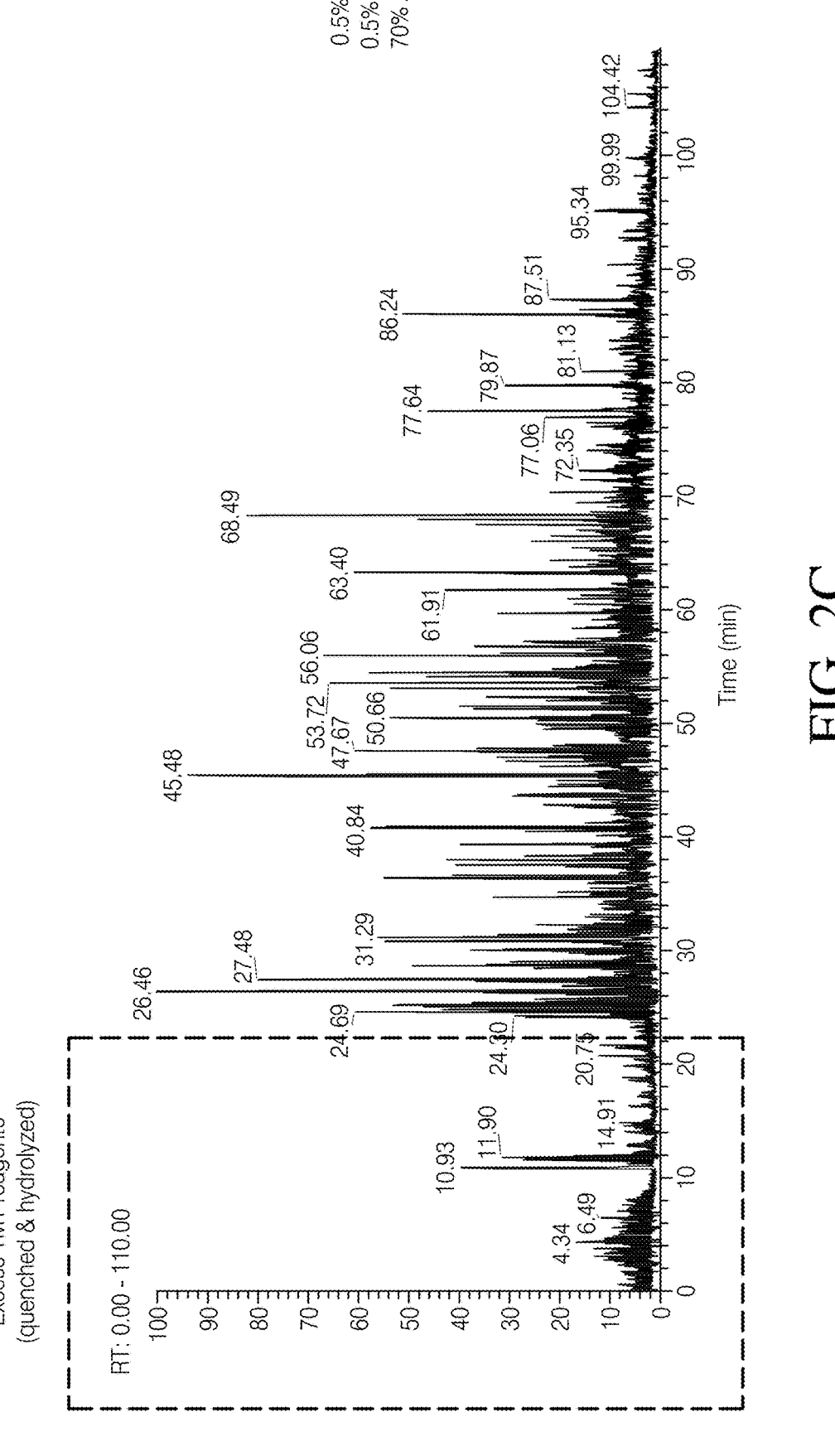
Figure 3A:
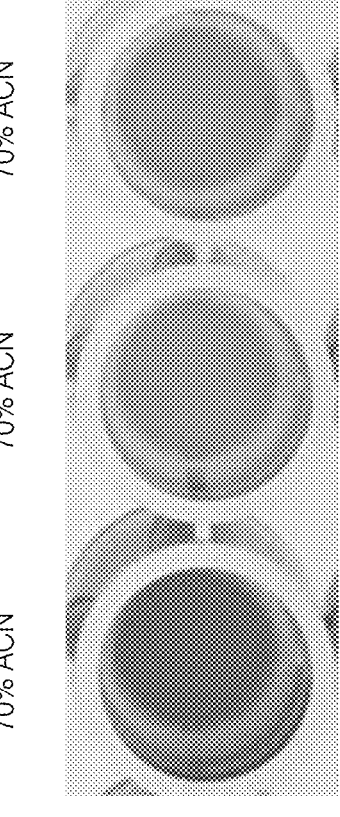
FIG. 3A shows a series of images from a quantitative colorimetric peptide assay for visual and spectroscopic assessment of peptide yield following clean-up. HeLa cell protein digests labeled with TMT reagent and cleaned-up with the Wash B solution containing 0.1% formic acid (A), Wash B solution containing 0.1% (v/v) formic acid and 0.1% (v/v) triethylamine (B), and Wash B solution containing 0.5% (v/v) formic acid and 0.5% (v/v) triethylamine (C).
Figure 3B:
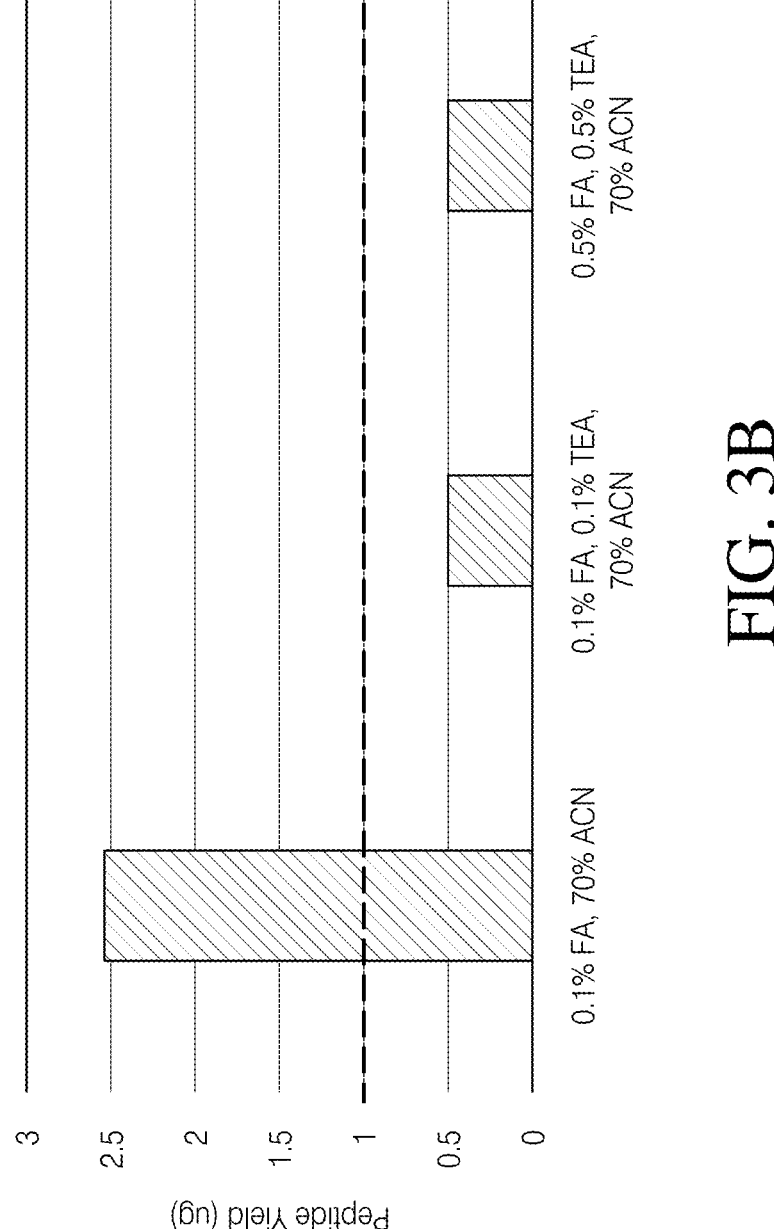
FIG. 3B is a bar graph comparing peptide yield for samples processed using the wash solutions described above. Due to presence of the residual TMT reagents, samples cleaned up with the Wash B solution (A) resulted in signal that was over five times that of the signal from samples treated with the buffers including TEA.
Figure 4A:
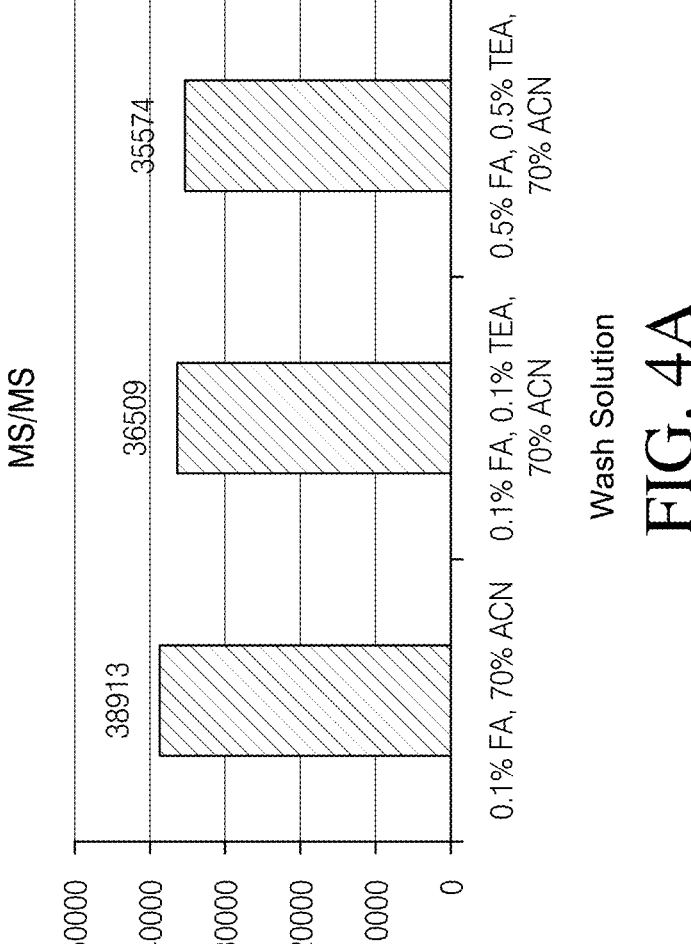
FIG. 4A shows number of MS/MS spectra acquired from LC-MS analysis of TMT-labeled peptide samples washed with different wash solutions.
Figure 4B:
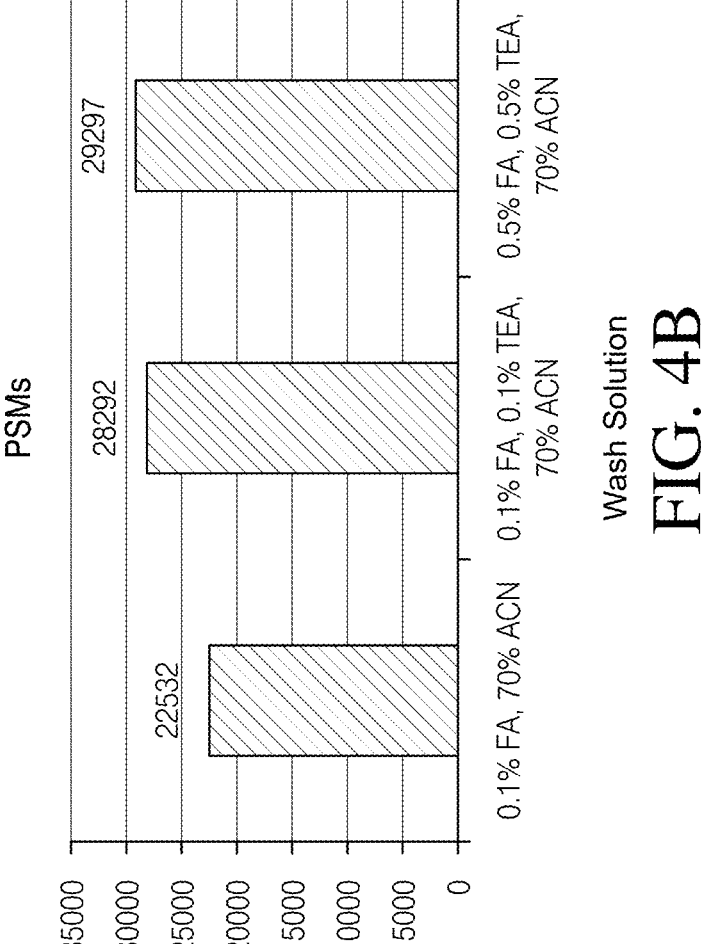
FIG. 4B shows number of peptide spectral matches (PSMs) identified from LC-MS analysis of TMT-labeled peptide samples washed with different wash solutions.
Figure 4C:
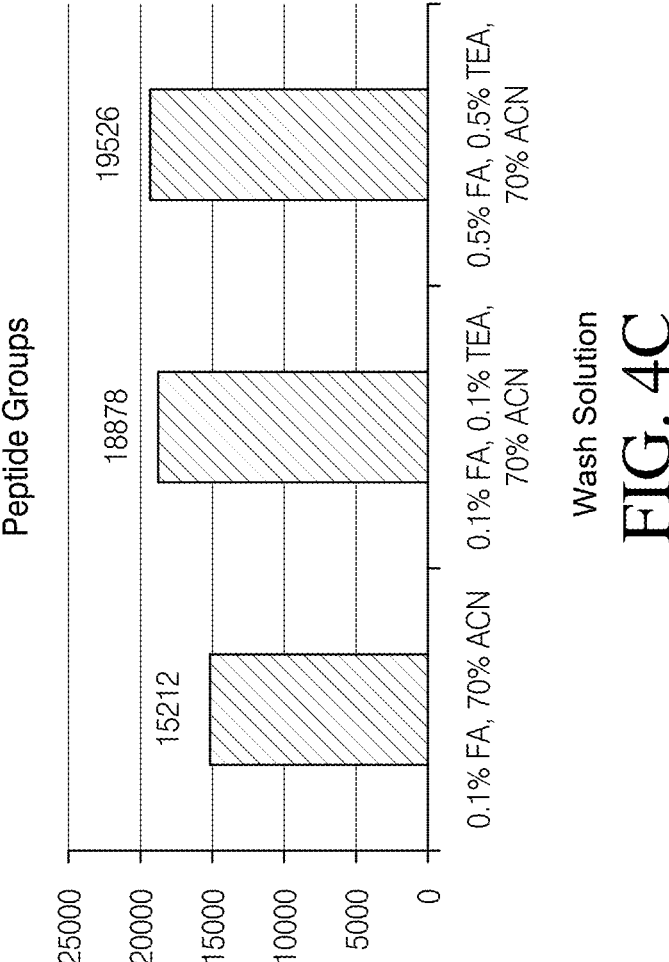
FIG. 4C shows number of unique peptides identified from LC-MS analysis of TMT-labeled peptide samples washed with different wash solutions.
Figure 4D:
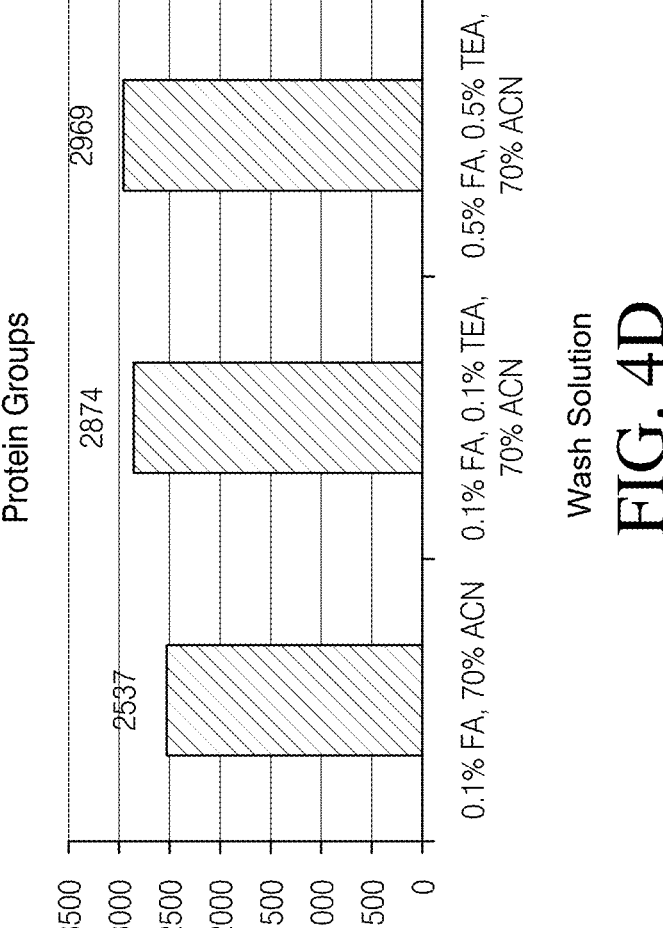
FIG. 4D shows number of protein groups identified from LC-MS analysis of TMT-labeled peptide samples washed with different wash solutions.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "about", when used to describe a numerical value, encompasses a range up to ±15% of that numerical value, unless the context clearly dictates otherwise.

While compositions and methods are described in terms of "comprising" various components or steps (interpreted as meaning "including, but not limited to"), the compositions and methods can also "consist essentially of" or "consist of" the various components and steps, such terminology should be interpreted as defining essentially closed-member groups.

"Biological sample," as used herein, refers to hematological, cytological and histological specimens, such as cells, cell cultures, single-celled organisms (e.g. yeast and bacteria), 3D cell cultures (e.g. spheroids and organoids), tissues, whole organisms (e.g. flies or worms), cell-free extracts, or a fluid sample (e.g., blood, serum, plasma, or sputum). A biological sample can refer to a sample that has been processed by filtration and/or centrifugation and can include supernatants of cell cultures and homogenized tissue or broken up cells. A tissue specimen can be any type of nervous, epithelial, muscular, or connective tissue, including an organ tissue. Tissue specimens can be fresh, frozen, fixed or preserved using common histological techniques. Biological samples can be from a plant or animal (e.g., human, mouse, fly, worm, fish, frog, fungi, and the like).

"Purifying" or "purification," as used herein, refers to the preparation of a peptide, a polypeptide, or a protein, in pure or substantially pure form. Purifying also refers to the removal of contaminants from a sample, including a contaminant originating from the sample or a contaminant which is introduced during sample handling. In particular, formulations and methods are provided herein for the removal of hydrophobic, hydrophilic and cationic contaminants from a biological sample. A sample of peptides or polypeptides is considered pure or substantially pure if non-peptide and non-polypeptide compounds have essentially been removed (i.e., peptides are the only analytes above the detection level), as measured by mass spectrometry and/or UV/vis spectroscopy. A sample is considered pure or substantially pure if the level of purified peptides and polypeptides in the sample is at least 70%, more preferably at least 80%. In some embodiments, the level of purified peptides and polypeptides is greater than about 80%; or greater than about 90%; or greater than about 95%. In some embodiments, the sample includes no contaminants (i.e., the level of purified peptides and polypeptides is 100%). If the sample is in liquid form, the level of purity is assessed in terms of a weight/volume (w/v) percentage. If the sample is in solid (e.g., lyophilized) form, the level of purity is assessed in terms of a weight/weight (w/w) percentage.

"Peptide" and "polypeptide", as used herein, are used interchangeably to refer to a polymer chain formed from two or more amino acid residues, where pairs of amino acid residues are covalently bonded through a peptide bond. As used herein, a peptide includes from 2-50 amino acids.

Peptides can include post-translational or other types of modifications, including, but not limited to, phosphorylation, glycation, glycosylation and methylation. A "peptide," as used herein, can refer to a single peptide compound or a mixture of two or more peptide compounds. A "peptide," as used herein, can be chemically synthesized by the condensation reaction of the carboxyl group of one amino acid to the amino group of another. As used herein, "peptide" also can be generated by digestion of a protein using a proteolytic enzyme (e.g., trypsin, Lys-C, AspN, or GluC) or chemical reaction which selectively hydrolyzes protein amide bonds. A peptide also can have one or more charges or potentially charged groups (depending on pH) at the N-terminus, C-terminus and/or side chains. Upon digestion with a proteolytic enzyme, proteins will yield peptides carrying at least one charge, and peptides often will carry at least two positive charges. Because the peptide includes one or more charges or potentially charged groups at the N-terminus, C-terminus and/or side chains, one or more cations and/or one or more anions are typically associated with the peptide or polypeptide to keep the compound electrostatically neutral. Representative examples of counterions include alkaline metal ions, alkaline earth metal ions, halogenides, sulfates, carbonates, phosphates, and acetates.

"Mass tag" and "tandem mass tag", as used herein, are used interchangeably to refer to a chemical labeling reagent containing one or more stable isotopes which can be distinguished by mass spectrometry analysis. A "mass tag" also refers to a set of reagents of the same chemical structure but different numbers of stable isotopes or isotopologues. A "mass tag" also can refer to a set of reagents of the same chemical structure and same numbers of stable isotopes but different distribution within the chemical structure, which can be differentiated by mass after gas-phase fragmentation in a mass spectrometer. A "mass tag," as used herein, further refers to a set of reagents that can be used to covalently label molecules in two or more samples. The two or more samples can be combined into one sample for mass spectrometry analysis. In some embodiments, a "mass tag" can be used to covalently label nucleic acids, peptide, carbohydrates, lipids or other small molecules derived from biological samples.

Methods, formulations and kits are described for purifying peptides and proteolytic digests derived from biological samples, such as tissues, cells and biological fluids. In general, methods and formulations are described herein to remove contaminants from peptides derived from a biological sample. Samples derived from biological specimens can contain a variety of hydrophobic, hydrophilic, and ionic contaminants. Contaminants can originate from the biological sample itself or be introduced during processing of the biological sample. The described methods implement a series of washing steps to remove unwanted contaminants from the sample. A particular advantage of the methods and associated wash solutions disclosed herein over known purification methods is that both hydrophobic and hydrophilic monovalent cationic contaminants (regardless of origin) can be removed from the sample. Thus, high purity peptides can be provided that are sufficiently free of contaminants. The isolated peptides are suitable for use in demanding downstream applications and assays that require extremely pure samples (e.g., LC-MS). Removal of undesirable debris and components from the biological sample (e.g., salts, fats, lipids, sugars, and the like) can prevent damage to the instrument and improve the quality of MS proteomics data (e.g., by removing unwanted ions). For example, when used in LC-MS applications, peptides purified according to the instant methods can minimize chromatographic interference, ionization suppression, and clogging of the liquid chromatography (LC) plumbing components. In addition, removal of contaminants can improve LC-MS peptide and protein identification rates through decreased sample complexity in the gas phase with fewer charge states (e.g. M+, M+2, M+3, etc.) and/or charge species (e.g. M+Na, M+2Na, etc.). Improved LC-MS spectral quality also can improve peptide and protein identification rates during data analysis using database searching, spectral library matching, or de novo sequencing.

The described methods and formulations improve over existing purification methods that implement standard reversed-phase and cation-exchange chromatography resins. As discussed above, a drawback of reversed-phase desalting methods is that hydrophobic molecules, such as lipids and detergents, can remain bound to the resin by hydrophobic interactions. Upon eluting the bound peptides from the resin with acidic solution containing organic solvent, the hydrophobic molecules also can elute and thereby contaminate the peptide sample. In order to address some of the shortcomings associated with use of reversed-phase resins for purification of peptides from biological samples, strong cation-exchange resins can be used as an alternative to reversed-phase approaches for peptide sample clean-up.

In one representative method using a cation-exchange resin, the sample is acidified and loaded onto a cation-exchange resin in an aqueous solution. Hydrophilic anionic and neutral species pass through the resin, while all cationic and hydrophobic species remain bound to the resin by ion-exchange or hydrophobic interactions, respectively. The resin is then washed with a first acidic aqueous solution of low ionic strength (e.g., 0.1% formic acid in water) to remove any excess hydrophilic cations from the resin matrix. The resin next is washed with a solution of the same ionic strength and acidity, but with an organic solvent component (e.g., 0.1% formic acid in 70% acetonitrile). The second wash solution removes neutral and anionic hydrophobic species (e.g., lipids, detergents, and the like) that are bound to the resin by hydrophobic interactions. After treatment with the second wash solution, only cationic species from the sample remain bound to the resin (e.g., atomic cations such as sodium, various small/large amines, and peptides). Peptides then are eluted with a basic solution containing an organic solvent component to eliminate any hydrophobic interactions, at high pH to ionize carboxylic acid groups on the peptides and to reduce the affinity of the amino-groups towards the resin. In addition, it is preferred that the ionic strength of the elution solution be sufficient (e.g., 0.1% (v/v) or greater) to compete for cation-exchange binding sites with the peptide amino groups. A representative elution solution can include a combination of ammonia or trimethylamine (TEA) in 30% or higher acetonitrile (ACN) organic solvent.

It is important to note here that all peptides produced from proteolytic digestion with trypsin contain at least two positive charges at low pH, at the N-terminus and at lysine/arginine residues of the C-terminus. Both monovalent and divalent cations can remain bound to the cation-exchange resin, but divalent cationic peptides have higher affinity for the strong cation-exchange resin than a cationic species with a single positive charge. As a result, undesired non-peptide cations are eluted from the resin together with the peptides. To address this problem, an improved method and wash solution is described herein that removes non-peptide singly charged cationic species from the resin, while concurrently removing neutral and anionic hydrophobic species (e.g., lipids, detergents, and the like) that are bound to the resin by hydrophobic interactions. Unexpectedly, by optimizing the ionic strength of the wash solution with various formulations of a volatile salt under acidic pH conditions, it was feasible to simultaneously maximize the removal of the undesired cations, while maintaining retention of peptides on the resin. As such, the described formulations and methods provide a significant improvement over existing methods for purifying peptides from biological samples.

In one aspect, methods are provided for isolating peptides of high purity from a biological sample, where the isolated peptides are substantially free of contaminants. The methods include a series of washing steps to remove unwanted species that can contaminate the purified peptide sample. Washing of the resin refers to a procedure where stationary phase resins or other solid materials used for chromatography are contacted by liquid mobile phase component. Washing of chromatographic supports can be accomplished by incubation and/or mixing of the resin with the wash buffers. Washing can also be accomplished by passing wash buffers through resins in a column format using centrifugation, vacuum, gravity, positive pressure or other means. A particular advantage of the methods disclosed herein over known purification methods is that both hydrophobic and hydrophilic monocationic contaminants can be removed from the peptide sample. The purified peptides are sufficiently pure for interrogation in further down-stream assays and applications that benefit from extremely pure samples. Examples of downstream applications include, but not limited to, Western blotting, immunoprecipitation/purification, ligand receptor binding assays, NMR spectroscopy, colorimetric and fluorometric qualitative and quantitative assays and LC-MS analysis. It was found, for example, that the purity of the peptides resulting from the improved process can significantly enhance sample quality metrics relevant to LC-MS analysis (e.g., peptide and protein identifications, sampling success rates, and the like).

Methods described herein provide particular advantages in the context of purification of samples containing peptides labeled with mass tags for comparative (i.e., relative quantitation) analysis of peptide and protein samples. For example, peptide samples (either before or after clean-up) can be labeled at N-termini and lysine residue side chains with amine-reactive Tandem Mass Tag (TMT) reagents. TMT reagents are non-volatile monovalent cations at low pH. However, excess TMT reagent in the sample can interfere with colorimetric and MS-based assays. The methods disclosed herein provide for the removal of excess TMT reagent from the sample. Removal of TMT reagent leads to a significant reduction of spectral interferences in the MS-based analyses, and reduced interferences in the quantitative colorimetric assay measurements of the sample peptide yields, resulting in improved peptide and protein identification numbers.

The biological sample can include a peptide (e.g., a peptide resulting from the digestion of a protein or polypeptide), as well as residual components from the biological sample and/or species remaining from the processing of the sample. Contaminants can include hydrophilic and/or a hydrophobic species, as well as charged species. For example, the biological sample can be contaminated with salts, detergents, lipids, nucleic acids, and other types of small molecules (e.g., carbohydrates, metabolites, nucleotides, etc.). The sample can include cationic and/or anionic species. In some embodiments, the sample can include monovalent and/or divalent cationic species. In other embodiments, the sample includes a hydrophilic contaminant (e.g., a neutral or ionic species) in addition to the monovalent and/or divalent cationic species. Examples of hydrophilic contaminants include, without limitation, salts, nucleic acids, and carbohydrates. Representative examples of monovalent cationic contaminants include ammonium, sodium, potassium, tris(hydroxymethyl)aminomethane (TRIS), hydroxylamine, ethanolamine, HEPES (4-(2-hydroxyethyl)-1-piperazineethanesulfonic acid), PIPES (piperazine-N,N'-bis(2-ethanesulfonic acid)), EPPS (4-(2-hydroxyethyl)-1-piperazinepropanesulfonic acid), and glycine.

In certain embodiments, the protein digest or peptide can be derivatized with a mass tag or other labeling reagent, such as, e.g., amine-, sulfhydryl-, carboxyl- and carbonyl-reactive Mass Tag (TMT™) reagents (available from Thermo Fisher Scientific; Waltham, MA), iTRAQ™ isobaric, eptide-tagging reagents (available from SCIEX; Framingham, MA), N, N-dimethyl leucine (di-Leu) reagents, combinatorial mass tags, fluorescent dyes, biotinylating reagents, and the like). Labeling with mass tags or other labeling reagents can introduce contaminants into the sample, for example in the form of the excess unreacted labeling reagents. For protein digest or peptide samples labeled with a mass tag (e.g., TMT) or other labeling reagent, the sample prior to purification can include residual mass tag, as well as components used in the labeling and quenching reactions (e.g., buffer salts). The contaminant can be unreacted mass tag or label. Alternatively, the contaminant can form during the labeling reaction. In some embodiments, the contaminant is derivative of the label or mass tag that is formed during the process of labeling the peptide or protein digest. In some embodiments, the mass tag derivative can be in the form of a monovalent cation. For example, monovalent cationic derivatives of mass tags such as TMT can include, e.g., NHS esters of unreacted TMT reagents, acid derivatives of TMT reagents formed by hydrolysis of the mass tag; and amide derivatives of TMT formed upon reaction of the mass tag with an amine or amine-containing compound.

One embodiment of the method is used to purify biological samples, such as peptides or protein digests, by washing the sample bound to a purification resin with a single solution to remove monovalent cationic and hydrophobic contaminants. Processed biological samples can contain hydrophobic components, such as externally introduced detergents that help with protein solubilization, and buffer salts, typically introduced to maintain pH and solubilization properties of proteins. After proteolytic digestion of the sample proteins, removal of these contaminants is critical to achieve optimal analysis by mass spectrometry and other analytical techniques. In one representative method, the sample is loaded onto a hydrophobic, polymer-based cation exchange material under acidic conditions (e.g., pH~1-5). Typically, the cation exchange material is contained within a column to facilitate easy handling and processing of the sample. Under acidic conditions, the sample can bind to the cation exchange material. In the next step of the process, the cation exchange material is washed with an acidic solution (e.g., pH~1-5). In certain embodiments, the pH is about 2-4. The acidic solution can include water and one or more volatile components, such as a volatile organic solvent and a volatile salt. The volatile salt can include a volatile acid (e.g., formic acid, acetic acid, trifluoroacetic acid, or trichloroacetic acid) and a volatile base (e.g., trimethylamine, ammonia, triethylamine, piperidine, or butylamine). Typically, the acidic solution can include 20% or greater (v/v) volatile organic solvent (e.g., acetonitrile, methanol, ethanol, n-propanol, iso-propanol, or acetone). For example, the acidic solution can include about 20%-40%; 40%-60%; 60%-80%; or greater than 80% (v/v) volatile organic solvent. The acidic solution can further include a volatile salt. The amount of volatile salt in the solution can be adjusted to maintain pH at a desired level. For example, to maintain the pH of the solution at ~1-5, the concentration of volatile salt can range from about 0.01% to about 1.0% (v/v). In some embodiments, the acidic solution includes water, 60% or greater (v/v) volatile organic solvent (e.g., acetonitrile, methanol, ethanol, n-propanol, iso-propanol, or acetone) and about 0.1% to 1.0% (v/v) volatile salt (e.g., a salt that includes a volatile acid component, such as formic acid, acetic acid, and/or trifluoroacetic acid, and a volatile base, such as ammonia, triethylamine, and/or piperidine), such that the pH of the solution is maintained at ~pH 2-4. In some embodiments, one or more volatile acids or volatile bases can be used. Upon treatment with the acidic solution, peptides are retained on the cation exchange material, and the monovalent cationic and/or hydrophobic contaminant can be removed from the cation exchange material. The retained peptides then can be eluted from the cation exchange material with an alkaline or neutral solution. The alkaline or neutral solution can include a combination of a volatile organic solvent and water. In certain embodiments, the elution solution includes 20% or greater (v/v) volatile organic solvent (e.g., 20%-40%; 40%-60%; 60%-80%; or greater than 80% (v/v)). Typically, the alkaline or neutral solution has a pH of 5 or greater. In certain embodiments, the solution has pH of greater than 7; greater than 8; greater than 9; greater than 10; or greater than 11. In addition, the alkaline or neutral solution can include a volatile base and/or volatile salt, as described herein. The amount of volatile salt in the elution solution can be adjusted to maintain pH at a desired level. To maintain the pH of the elution solution at 5 or greater, the concentration of volatile salt can range from about 0.01% to about 1.0% (v/v). In some embodiments, the elution solution includes 40% or greater (v/v) volatile organic solvent (e.g., acetonitrile, methanol, ethanol, n-propanol, iso-propanol, or acetone) and about 0.01% to 1.0% (v/v) volatile salt (e.g., a salt that includes a volatile acid component, such as formic acid, acetic acid, and/or trifluoroacetic acid, and a volatile base, such as ammonia, triethylamine, and/or piperidine, such that the pH of the solution is maintained at ~pH 8-12.

One exemplary method provided herein is used to purify biological samples, such as peptides or protein digests. The method includes washing a sample that is bound to a resin with a more than one solution to first remove hydrophobic and monocationic contaminants and then subsequently to remove hydrophilic contaminants. For example, a sample may contain a high concentration of a preservative, such as a carbohydrate, which, if not sufficiently removed, can pose a significant level of interference in the downstream analysis of the sample by MS. Efficient removal of such contaminants typically require use of wash solutions that include 20% or less (v/v) volatile organic solvent. Therefore, for certain samples, it can be advantageous to include multiple wash solutions to remove hydrophilic, hydrophobic and ionic contaminants from the sample. In one representative method that implements multiple wash solutions, the sample include peptides is loaded onto the cation exchange material, as disclosed herein. The material then is washed with a first acidic solution (pH~2-4). In some embodiments, the first acidic solution includes 20% or less (v/v) volatile organic solvent, water, and a volatile acid. In some embodiments, the first acidic solution includes 10%-20%; or 5%-10%; or 1%-5%; or less than 1% (v/v) volatile organic solvent. In some embodiments, the first acidic solution includes less than 5% (v/v) volatile organic solvent and about 0.01% to 0.5% (v/v) volatile acid (e.g., formic acid, acetic acid, trifluoracetic acid, or trichloroacetic acid), such that the pH of the solution is maintained at ~pH 2-4. Treatment with the first acidic solution removes the hydrophilic contaminant from the cation exchange material yet allows the peptide to remain retained on the cation exchange material. The cation exchange material then is washed with a second acidic solution (e.g., pH~1-5) to remove the monovalent cationic and/or hydrophobic contaminants from the cation exchange material, while the peptide stays bound to the cation exchange material. The second acidic solution can include water and one or more volatile components, such as a volatile organic solvent (e.g., (e.g., acetonitrile, methanol, ethanol, n-propanol, iso-propanol, or acetone) and a volatile salt (e.g., a salt formed from a volatile acid, such as formic acid, and a volatile base, such as trimethylamine). Typically, the second acidic solution includes 20% or greater (v/v) volatile organic solvent. For example, the acidic solution can include about 20%-40%; 40%-60%; 60%-80%; or greater than 80% (v/v) volatile organic solvent. In some embodiments, the acidic solution includes greater than 60% (v/v) volatile organic solvent and about 0.01% to 1.0% (v/v) volatile salt, such that the pH of the solution is maintained at ~pH 2-4. The retained peptide can be eluted from the cation exchange material using an alkaline or neutral solution, as disclosed herein.

A representative method for isolating a pure peptide from a biological sample using formulations and methods disclosed herein is illustrated in FIG. 1. Referring to FIG. 1, the peptide purification workflow 100 involves digesting a biological sample using methods that are well known to those skilled in art to provide a crude digest sample 110 containing digested biological material (e.g., cells, tissue, nucleic acids, proteins, polypeptides, lipids, carbohydrates, and the like) and one or more contaminants, such as salts, detergents, lipids and other small neutral molecules. The digested sample 110 is acidified by the addition of neat or diluted acid solution sufficient to reduce the pH to 1-4. Digested sample 110 then is transferred onto a hydrophobic, polymer-based cation exchange material 115 (Step 1). The cation exchange material can be contained within clean-up column 116 fitted with an exit port 117. The column can be contained within a centrifuge tube 118. The centrifuge tube containing clean-up column can be centrifuged under vacuum to allow components 120 (e.g., digested biological material) from the sample to flow through resin 115 contained in column 116. Components 120 having little or no affinity for cation exchange material 115 flow through the cation exchange material, exit through port 117, and collect in centrifuge tube 118. A first acidic solution (Wash Solution A) is applied to the cation exchange material and centrifuged under vacuum, thereby washing hydrophilic contaminants (e.g., neutral and anionic components) 130 through the cation exchange material, while cationic and hydrophobic species (e.g., peptides and/or digested protein) are retained on cation exchange material 115 (Step 2). Hydrophilic contaminants 130 are discarded. A second acidic solution (Wash Solution B) is applied to the cation exchange material, and the column is centrifuged under vacuum to remove hydrophobic (e.g., neutral, anionic and monovalent cationic) and hydrophilic monovalent cationic contaminants 140 from resin 115 (Step 3). Divalent cationic species are retained on the cation exchange material, while the monovalent cationic and/or hydrophobic contaminants 140 are removed from the cation exchange material by centrifugation under vacuum. Because peptides produced by enzymatic digestion of a polypeptide or protein have at least two positive charges (i.e., divalent cations), the peptides are retained on the cation exchange material 115 after Step 3. The peptides then are eluted from the cation exchange material with an alkaline or neutral solution (Step 4) to provide a purified peptide solution 150. The purified peptide solution 150 optionally can be dried (e.g., by lyophilization) (Step 5) to provide dried peptide 160 that is sufficiently pure for use in further downstream applications.

One embodiment of the method involves purifying biological samples, such as peptides or protein digests, by washing the sample bound to a purification resin with more than one solution to remove hydrophilic contaminants before hydrophobic and monovalent cationic contaminants. In yet another method, the sample containing peptides is loaded onto the cation exchange material, as disclosed herein. The cation exchange material then is washed with a first acidic solution, wherein the first acidic solution includes greater than 20% (v) volatile organic solvent, water, and a volatile salt, such that the peptide-containing compound is retained on the cation exchange material and the monovalent cationic and/or hydrophobic contaminant is removed from the cation exchange material.

The first acidic solution can include water and one or more volatile components, such as a volatile organic solvent and a volatile salt. Typically, the first acidic solution includes 20% or greater (v/v) volatile organic solvent. For example, the acidic solution can include about 20%-40%; 40%-60%; 60%-80%; or greater than 80% (v/v) volatile organic solvent. In some embodiments, the acidic solution includes greater than 60% (v/v) volatile organic solvent and about 0.01% to 1.0% (v/v) volatile salt, such that the pH of the solution is maintained at ~pH 2-4. Next, a second acidic solution is used to wash the cation exchange material. In certain embodiments, the second acidic solution includes 20% or less (v/v) volatile organic solvent, water, and a volatile acid. Treatment with the second acidic solution removes the hydrophilic contaminant, yet allows the peptide to remain on the cation exchange material. In some embodiments, the second acidic solution includes 20% or less (v/v) volatile organic solvent, water, and a volatile acid. In some embodiments, the first acidic solution includes 10%-20%; or 5%-10%; or 1%-5%; or less than 1% (v/v) volatile organic solvent. In some embodiments, the first second solution includes less than 5% (v/v) volatile organic solvent and about 0.01% to 0.5% (v/v) volatile acid, such that the pH of the solution is maintained at ~pH 2-4. The retained peptide can be eluted from the cation exchange material using an alkaline or neutral solution, as disclosed herein.

In another aspect, the methods provided herein further include steps for labeling the protein digest or peptide with a labeling reagent (e.g., mass tag). Addition of components (e.g., buffer salts, quench reagents, and residual labeling reagent) to facilitate labeling of proteins, protein digests and peptides with mass tags can introduce further contaminants into the biological sample that can degrade the quality of LC-MS data and/or damage chromatography columns and pumps. Advantageously, the formulations and methods provided herein can remove contaminants introduced during the labeling process to provide peptides labeled with mass tags or other labeling reagents substantially free of such contaminants and suitable for analysis using LC-MS systems. The methods provided herein can remove excess TMT reagent from the sample, thus leading to a significant reduction of spectral interferences in the MS-based analyses, reduced interferences in the quantitative colorimetric assay measurements of the sample peptide yields (as the TMT reagent interferes with these types of assays), and reduction in the physical deposition and accumulation of these materials on the LC-MS instrument components, which ultimately prolong the high sensitivity of an instrument system and leads to improved peptide and protein identification numbers.

Mass tags include, for example, tandem mass tag reagents such as the TMT and TMTPRO Label Reagents, commercially available from Thermo Fisher Scientific (Waltham, MA). In certain embodiments, the protein digest is labeled with the mass tag before peptide cleanup. In other embodiments, peptides can be labeled with TMT reagent after peptide clean up.

Thus, provided herein are methods that further include labeling of the protein digest or purified peptide with a TMT reagent. A representative method for labeling a protein digest with TMT reagent includes combining a protein digest dissolved in a slightly basic (e.g. pH 7.5-9) buffered (e.g. 100 mM TEAB or HEPES) solution with TMT reagent dissolved in an organic solvent (e.g. acetonitrile), incubating the mixture at room temperature; and then quenching the labeling reaction using a solution containing a primary amine (e.g., hydroxylamine).

A representative method for labeling a purified peptide with TMT reagent includes dissolving a dried peptide sample in slightly basic (e.g. pH 7.5-9) buffered (e.g. 100 mM TEAB or HEPES) solution. The dissolved peptide sample then is combined with TMT reagent dissolved in acetonitrile and incubated at room temperature. The labeling reaction is quenched with a solution containing hydroxylamine. Once quenched, the labeled sample is acidified with TFA (pH<3) and desalted.

The methods provided herein implement a solid phase extraction resin. The extraction resin can include a hydrophobic, polymer-based cation exchange material. Such materials are well known to those in the art, and various cation exchange resins can be used in the practice of the disclosed method. Representative examples of suitable hydrophobic, polymer-based cation exchange materials include sulfonated divinyl benzene polystyrene, sulfonated polydivinyl benzene resins, sulfonated polydivinyl benzene/polystyrene resins, and sulfonated polydivinyl benzene/polystyrene resins. Representative examples of commercially available hydrophobic, polymer-based cation exchange materials include, Oasis MCX sorbent and POROS™ XS Strong Cation Exchange Resin available from Waters Corporation (Milford, MA), and Thermo Fisher Scientific (Bedford, MA), respectively. In some embodiments, the extraction resin can include a combination of cation exchange materials. In certain embodiments, the purification resin is a physical blend of cation exchange materials. In certain embodiments, the extraction resin can be or include a copolymer formed from a combination of monomers, such as, e.g., divinyl benzene or styrene, and pyrrolidone monomers. In some embodiments, the cation exchange material is a copolymer of pyrrolidone and a sulfonated monomer, such as divinyl benzene or sulfonated polydivinylbenzene. In certain embodiments, other types of hydrophobic and/or hydrophilic resins with or without strong-cation exchange properties (e.g., C18 resins, non-sulfonated polydivinyl benzene/polystyrene resins, silica, agarose, sepharose, and the like) can be combined (e.g., as a physical blend) with a hydrophobic polymer-based cation exchange material, as disclosed herein. In certain embodiments, the extraction resin is a combination of a strong cation exchange material (e.g., a sulfonated monomer, as disclosed herein) and a hydrophilic and/or hydrophobic resin. In certain embodiments, the binding mode of the hydrophilic and/or hydrophobic resin has the same binding mode as the strong cation exchange material.

The solid-phase extraction (SPE) resin can be in the form of a magnetic particle (e.g., bead). For example the SPE resin can be composed of a polymeric material that further includes magnetic material. Application of a magnetic field to a sample containing an analyte bound to magnetic polymer particles allows the isolation of the analyte without the use of centrifugation or filtration By "magnetic" is meant herein that the polymer particles contain superparamagnetic crystals. Thus, the magnetic polymer particles are magnetically displaceable but are not permanently magnetizable. Many processes for preparing magnetic polymer particles are known, a large number of which involve preparing maghemite- or magnetite-containing polymer particles from pre-formed magnetic iron oxides, e.g. magnetite. Magnetic polymer particles can be implemented in the peptide purification protocols disclosed herein can be easily automated on a wide range of automation platforms.

The wash solutions provided herein utilize one or more volatile components, such as organic solvents, bases and salts. Volatile components are particular useful as they can be readily evaporated under vacuum without introducing additional contaminants into the sample. Volatile components are also useful as they are compatible with electrospray ionization-based mass spectrometry analysis. Representative examples of volatile organic solvents that can be used in the disclosed methods include, without limitation, acetonitrile, methanol, ethanol, n-propanol, iso-propanol, and acetone. In some cases, a combination of volatile organic solvents can be used in the disclosed methods. Representative examples of volatile salts that can be used in the disclosed methods can include a volatile acid and/or a volatile base. Suitable volatile bases include, e.g., trimethylamine (TEA), ammonia, piperidine, and butylamine. Suitable volatile acids include, e.g., formic acid, acetic acid, trifluoracetic acid, and trichloroacetic acid. In certain embodiments, the volatile salt includes a volatile base and a volatile acid, such as, ammonium acetate, ammonium formate, ammonium trifloroacetate, triethylammonium formate, triethylammonium acetate, triethylammonium trifluoroacetate or ammonium bicarbonate).

Further provided herein are kits for purifying a biological sample that includes a peptide. The kits can be used to isolate a peptide derived from a biological sample, such as a cell or tissue. The peptide can be generated by digestion of a protein or polypeptide.

In one aspect, kits are provided to perform efficient and reproducible processing of cells (e.g., cultured mammalian cells), biological fluids (e.g., plasma or serum) and tissues for proteomic MS analysis and other types of assays. Kits can include pre-formulated buffers, MS-grade enzyme mix, peptide clean-up (plates and columns), and an optimized time-efficient protocol to generate peptide samples that are compatible with LC-MS analysis. Purified peptide samples can be prepared in several hours (e.g., in less than four hours) using the kits and methods provided herein, thereby significantly reducing standard processing times associated with existing kits and methods. Protein samples from about 1 μg to about 10 mg or greater can be processed using the disclosed methods and kits to provide purified peptide samples in high yield. In some embodiments, the kits can be used to process protein samples in the range of about 0.5 mg to about 2 mg.

The kits provided herein can include pre-formulated buffers, MS-grade enzymes (e.g., nuclease, reduction/alkylation solution for cysteine modification, and trypsin/Lys-C protease mix for protein digestion), and a protocol to generate MS-compatible peptide samples. In addition, the kit can include a peptide clean-up plate or vial and solutions to prepare detergent-free peptide samples for direct LC-MS analysis or further sample processing such as isobaric tag (e.g., TMT™ Reagent) labeling, phosphopeptide enrichment or fractionation (e.g., high pH reversed-phase fractionation). In certain embodiments, kits provided herein can include one or more wash solutions, as described herein, and one or more additional components, such as, e.g., lysis solution, universal nuclease, reduction solution, alkylation solution, enzyme reconstitution solution, trypsin/Lys-C protease mix, enzymes, digestion stop solution, and elution solution.

A representative example of a kit for purifying a peptide originating from a biological includes: (a) a hydrophobic, polymer-based cation exchange material; (b) an acidic solution including a volatile salt, water and greater than 20% (v/v) volatile organic solvent; (c) a neutral or alkaline solution including a volatile base, water and a volatile organic solvent; and (d) instructions for using the kit to purify the biological sample.

Another example of a kit for purifying a peptide originating from a biological sample includes: (a) a hydrophobic, polymer-based cation exchange material; (b) an acidic solution including greater than 20% (v/v) volatile organic solvent, a volatile salt, and water; (c) an acidic solution including 20% or less (v/v) volatile organic solvent, a volatile salt, and water; (d) a neutral or alkaline solution including a volatile base, water, and a volatile organic solvent; and (e) instructions for using the kit to purify the biological sample.

The following examples are included to demonstrate certain embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

The examples provided herein utilize the following materials and general methods unless indicated otherwise. Additional materials were obtained from the following Thermo Fisher Scientific (Rockford, IL) or commercial sources where noted.

Example 1

Purification of TMT-Labeled Peptides

The following protocol describes a method to purify peptides labeled with TMT reagents. Peptides can be derived from a proteolytic digest of a biological sample (e.g., cultured cells, tissue, purified proteins, serum or plasma) and processed as described in EXAMPLE 3 until the dry peptide is obtained after vacuum centrifugation. Alternatively, C18 or another reversed phase solid phase extraction clean up material can be used to desalt the sample before vacuum centrifugation. Dried peptides are dissolved in suitable buffer (e.g. 100 mM TEAB pH 8.5 or 100 mM HEPES pH 8.0). Peptides from different samples labeled with TMT reagents. For 100 μg of peptide sample, 0.4-0.8 mg of TMT reagent in 40 μL of acetonitrile is used to label samples for 1 hour at room temperature. Reactions are stopped by adding 8 μL of 5% hydroxylamine and incubated for 5 minutes. TMT-labeled peptide samples are the acidified to pH 2-4 using 1-10% formic acid before or after combining into one sample. The combined sample is then loaded onto a clean-up column containing 50-100 mg of a hydrophobic, polymeric cation exchange material, as disclosed herein. Once loaded, the column is centrifuged at 1,000 rpm for 10 minutes. 3 mL of an acidic wash buffer, as described herein, is added, and the column is centrifuged at 2,000 rpm for 2 minutes to remove hydrophilic contaminants (e.g., neutral and anionic components). 3 mL of a second acidic wash buffer, as described herein, is added and the column is centrifuged at 2,000 rpm for 2 minutes. 3 mL of the second acidic wash buffer is again added and centrifuged at 2,000 rpm for 2 minutes to remove hydrophobic (e.g., neutral, anionic and monovalent cationic) and hydrophilic monovalent cationic contaminants. 3 mL of the elution solution, as described herein, is added into column and centrifuged at 2,000 rpm for 2 minutes to collect the clean peptide sample. The peptide sample is dried using a vacuum centrifuge. The sample can be resuspended in 100-500 μL of 0.1% formic acid in water for LC-MS analysis. Optionally, peptide yield and concentration can be assessed using a quantitative peptide assay such as the Pierce™ Quantitative Colorimetric Peptide Assay. For LC-MS analysis, 1-10 μg of peptide is adjusted with 0.1% formic acid in water solution to 0.1-1 μg/uL. Triplicate protein digest samples (1 μg per injection) were separated using a Thermo Scientific™ Dionex™ Ultimate™ 3000 Nano LC system using a 50 cm C18 Thermo Scientific EASY-Spray™ column with an acetonitrile gradient from 3% to 28% over 85 min, 28% to 45% over 30 min, at a flow rate of 300 nL/min on a Thermo Scientific™ Fusion™ Trbrid™ mass spectrometer using a top speed data dependent acquisition method. MS spectra were acquired using a resolution of 120K with a target value of 4e5 and 50 ms max injection time. MS/MS spectra were generated using CID NCE 35 a target value of 1e5 and 50 ms max injection time. MS/MS/MS spectra were generated using HCD NCE 60 at a resolution of 50K a target value of 1e5 and 105 ms max injection time. LC-MS data were analyzed using the SEQUEST® HT search engine in Thermo Scientific™ Proteome Discoverer™ 2.3 software using static carbamidomethyl (C), dynamic oxidation (M), TMT6plex or TMTpro (K, N-term), and deamidation (N, Q) modifications. Data were searched against the Uniprot human protein database and results were filtered using a 1% protein FDR threshold (see, FIG. 2A-FIG. 2C and FIG. 3A-FIG. 3B). The use of the improved acidic wash buffers containing a volatile salt (TEA and FA) compared to the standard buffer (FA only) effectively removed the excess quenched and hydrolyzed TMT reagents from the beginning MS chromatograms. In addition, removal of excess TMT reagents was also confirmed by reduction in the background signal measured using the colorimetric peptide assay. Removal of background signal related to excess TMT reagents is required for accurate peptide measurement for LC-MS analysis.

Example 2

Purification of TMT Reagent-Labeled Protein Digests from Biological Samples

The following protocol describes a method to isolate peptides from a biological sample (e.g., cultured cells, tissue, purified proteins, serum or plasma). Proteins are extracted, reduced and alkylated from the biological sample using methods that are well-known in the art. Reduced and alkylated proteins then are digested using a mixture of trypsin and Lys-C protease in suitable buffer (e.g. 100 mM TEAB pH 8.5 or 100 mM HEPES pH 8.0). Protein digests are from different samples labeled with TMT reagents. For 10 μg of peptide sample, 0.04-0.08 mg of TMT reagent in 20 μL of acetonitrile is used to label samples for 15 minutes to 1 hour at room temperature. Reactions are stopped by adding 1-4 μL of 5% hydroxylamine and incubated for 5 minutes. TMT-labeled peptide samples are the acidified to pH 2-4 using 1-10% formic acid before or after combining into one sample. TMT-labeled peptide samples are purified according to the following method. The combined sample is transferred to a dry peptide clean-up column containing a hydrophobic, polymeric cation exchange material, as disclosed herein. Once loaded, the column is centrifuged at 1,000 rpm for 10 minutes. 300 μL of an acidic wash buffer, as described herein, is added, and the column is centrifuged at 2,000 rpm for 2 minutes to remove hydrophilic contaminants (e.g., neutral and anionic components). 300 μL of a second acidic wash buffer, as described herein, is added and the column is centrifuged at 2,000 rpm for 2 minutes. 300 μL of the second acidic wash buffer is again added and centrifuged at 2,000 rpm for 2 minutes to remove hydrophobic (e.g., neutral, anionic and monovalent cationic) and hydrophilic monovalent cationic contaminants. 300 μL of the elution solution, as described herein, is added into column and centrifuged at 2,000 rpm for 2 minutes to collect the clean peptide sample. The peptide sample is dried using a vacuum centrifuge. The sample can be resuspended in 100 μL of 0.1% formic acid in water for LC-MS analysis. Optionally, peptide yield and concentration can be assessed using a quantitative peptide assay such as the Pierce™ Quantitative Colorimetric Peptide Assay. For LC-MS analysis, 1-10 μg of peptide is adjusted with 0.1% formic acid in water solution to 0.1-1 μg/uL. Triplicate protein digest samples (1 μg per injection) were separated using a Thermo Scientific™ Dionex™ Ultimate™ 3000 Nano LC system using a 50 cm C18 Thermo Scientific EASY-Spray™ column with an acetonitrile gradient from 3% to 28% over 85 min, 28% to 45% over 30 min, at a flow rate of 300 nL/min on a Thermo Scientific™ Fusion™ Tribrid™ mass spectrometer using a top speed data dependent acquisition method. MS spectra were acquired using a resolution of 120K with a target value of 4e5 and 50 ms max injection time. MS/MS spectra were generated using CID NCE 35 a target value of 1e5 and 50 ms max injection time. MS/MS/MS spectra were generated using HCD NCE 60 at a resolution of 50K a target value of 1e5 and 105 ms max injection time. LC-MS data were analyzed using the SEQUEST® HT search engine in Thermo Scientific™ Proteome Discoverer™ 2.3 software using static carbamidomethyl (C), dynamic oxidation (M), TMT6plex or TMTpro (K, N-term), and deamidation (N, Q) modifications. Data were searched against the Uniprot human protein database and results were filtered using a 1% protein FDR threshold. See, FIG. 4A-FIG. 4D. Removal of excess TMT reagents and other contaminants, using the improved wash buffers compared to the standard wash buffer reduced the total number of MS/MS scans but increased the total numbers of peptide spectral matches (PSMs), unique peptides and protein groups identified by LC-MS.

Example 3

Purification of Peptides from Biological Samples

Figure 5A:
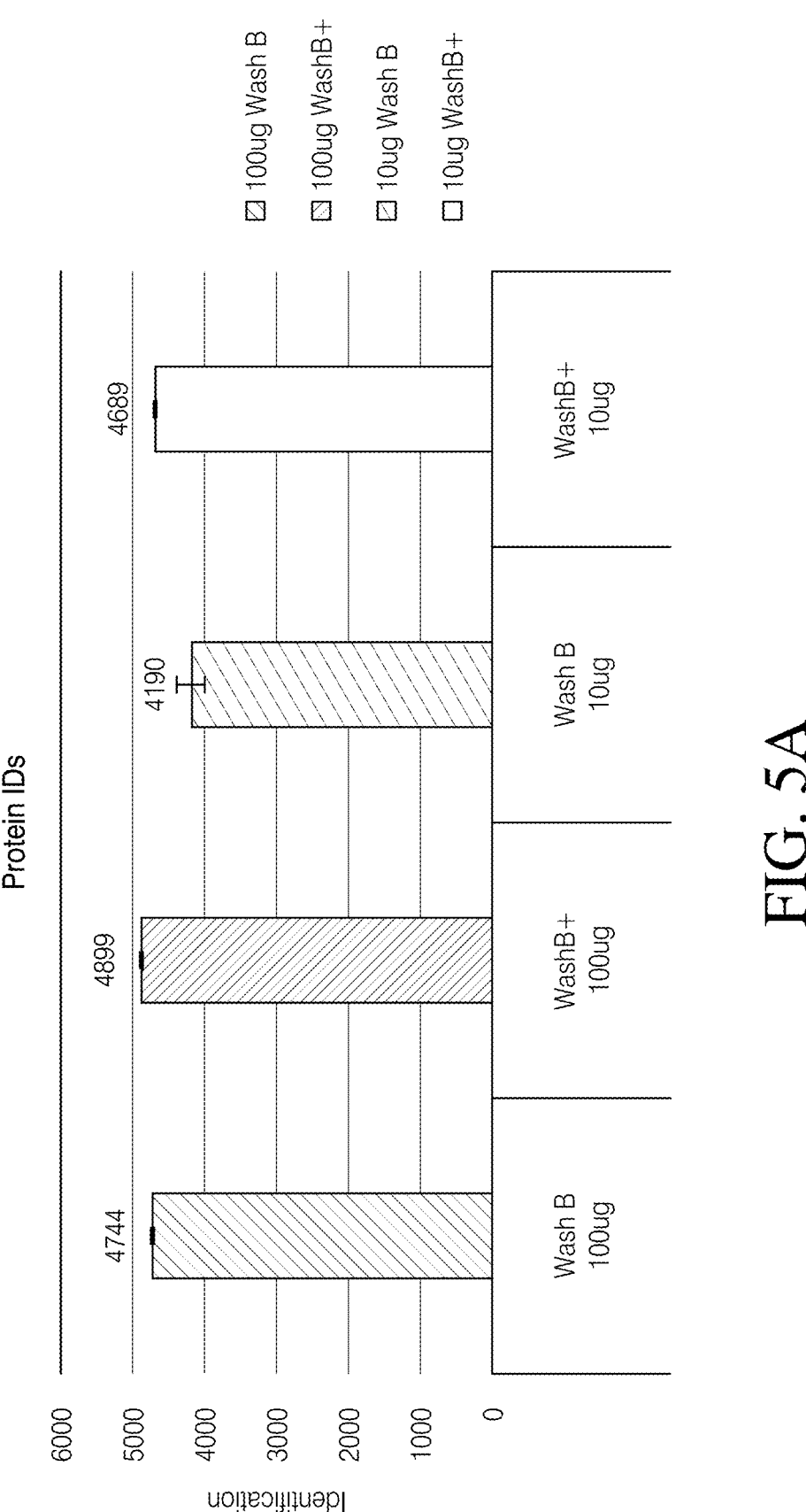
FIG. 5A shows protein groups identified from LC-MS analyses of different peptide sample amounts washed with different wash solutions.
Figure 5B:
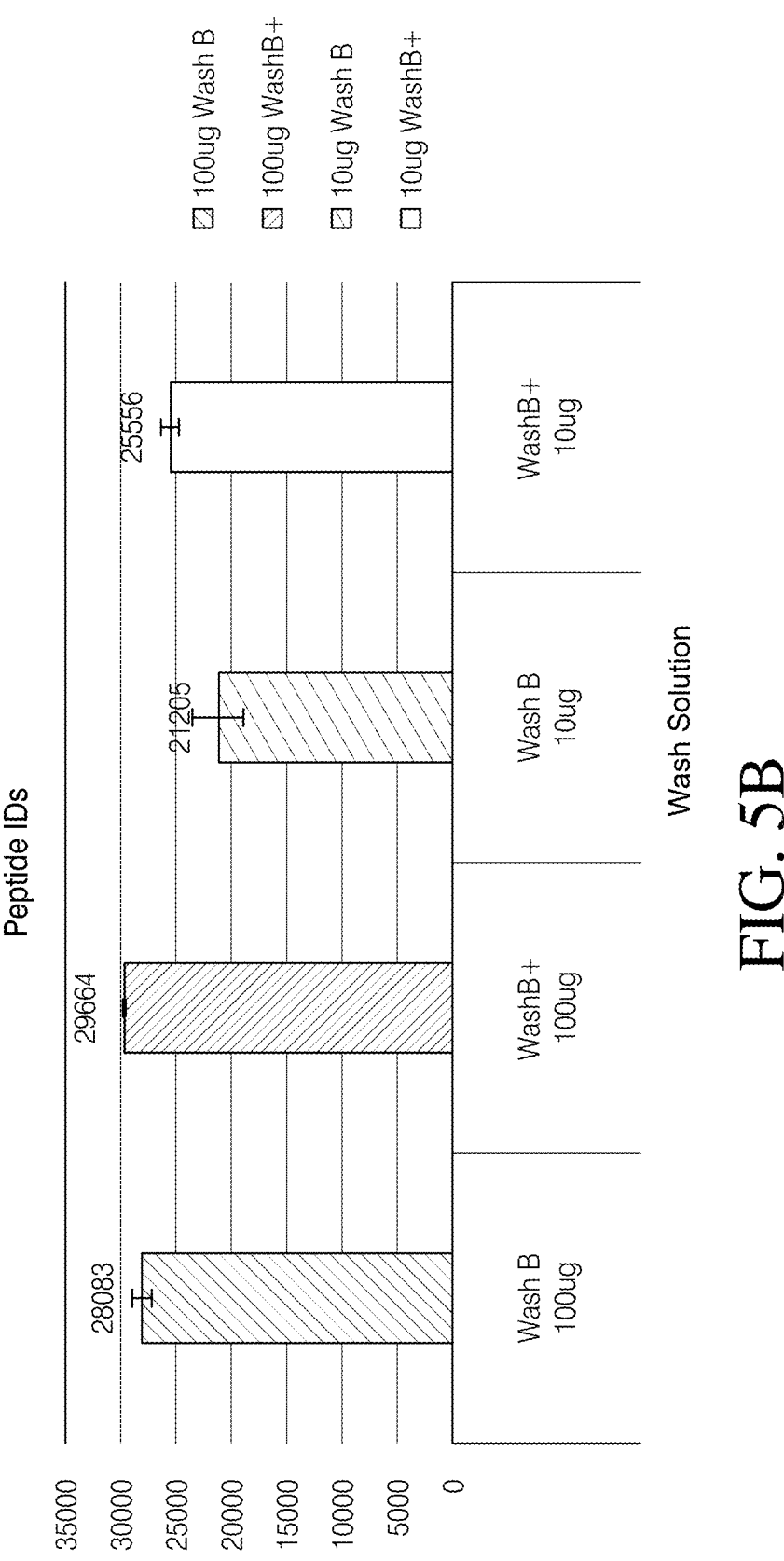
FIG. 5B shows unique peptides identified from LC-MS analyses of different peptide sample amounts washed with different wash solutions.

The following protocol describes a method to purify peptides from a proteolytic digest of a biological sample (e.g., cultured cells, tissue, purified proteins, serum or plasma). Proteins are extracted, reduced and alkylated from the biological sample using methods that are well-known in the art. Reduced and alkylated proteins then are digested using a mixture of trypsin and Lys-C protease. The digestion of proteins is stopped by addition of 1-10% formic acid until the pH range is 2-4. The protein digest sample is transferred to a dry peptide clean-up column containing 5-10 mg of a hydrophobic, polymeric cation exchange material, as disclosed herein. Once loaded, the column is centrifuged at 1,000 rpm for 10 minutes. 300 μL of an acidic wash buffer, as described herein, is added, and the column is centrifuged at 2,000 rpm for 2 minutes to remove hydrophilic contaminants (e.g., neutral and anionic components). 300 μL of a second acidic wash buffer, as described herein, is added and the column is centrifuged at 2,000 rpm for 2 minutes. 300 μL of the second acidic wash buffer is again added and centrifuged at 2,000 rpm for 2 minutes to remove hydrophobic (e.g., neutral, anionic and monovalent cationic) and hydrophilic monovalent cationic contaminants. 300 μL of the elution solution, as described herein, is added into column and centrifuged at 2,000 rpm for 2 minutes to collect the clean peptide sample. The peptide sample is dried using a vacuum centrifuge. The sample can be resuspended in 100 μL of 0.1% formic acid in water for LC-MS analysis. Optionally, peptide yield and concentration can be assessed using a quantitative peptide assay such as the Pierce™ Quantitative Colorimetric Peptide Assay. For LC-MS analysis, 1-10 μg of peptide is adjusted with 0.1% formic acid in water solution to 0.1-1 μg/uL. Triplicate protein digest samples (1 μg per injection) were separated using a Thermo Scientific™ Dionex™ Ultimate™ 3000 Nano LC system using a 50 cm C18 Thermo Scientific EASY-Spray™ column with an acetonitrile gradient from 3% to 28% over 85 min, 28% to 45% over 30 min, at a flow rate of 300 nL/min on a Thermo Scientific™ Q Exactive™ Plus Hybrid Quadrupole-Orbitrap™ mass spectrometer using a top 20 data dependent acquisition method. MS spectra were acquired using a resolution of 70K with a target value of 3e6 and 100 ms max injection time. MS/MS spectra were generated using HCD NCE 28 at a resolution of 17.5K a target value of 1e5 and 54 ms max injection time. LC-MS data were analyzed using the SEQUEST® HT search engine in Thermo Scientific™ Proteome Discoverer™ 2.3 software using static carbamidomethyl (C), dynamic oxidation (M), and deamidation (N, Q) modifications. Data were searched against the Uniprot human protein database and results were filtered using a 1% protein FDR threshold. FIG. 5A and FIG. 5B shows the results of the analysis in terms of peptide and protein identification numbers for 10 μg and 100 μg of Hela cell lysate sample prepared using a standard wash solution with 0.1% formic acid and 70% ACN (Wash B) and an improved wash solution (WashB+ including 0.5% formic acid, 0.5% trimethylamine, and 70% ACN). As shown in FIG. 5A and FIG. 5B, more proteins and peptides were identified using the improved wash solution that removes additional contaminants as compared to standard wash solution.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following clauses and claims define the scope of the invention and that methods and structures within the scope of these clauses and claims and their equivalents be covered thereby. Embodiments may be in accordance with following numbered clauses:

1. A method of purifying a biological sample, comprising:
(a) contacting the biological sample with a hydrophobic, polymer-based cation exchange material under acidic conditions, such that the sample binds to the cation exchange material, wherein the sample comprises:
(i) a peptide, and
(ii) a monovalent cationic contaminant and/or a hydrophobic contaminant;
(b) washing the cation exchange material with an acidic solution, wherein the acidic solution comprises greater than 20% (v/v) volatile organic solvent, water, and a volatile salt, such that the peptide is retained on the cation exchange material and the monovalent cationic and/or hydrophobic contaminant is removed from the cation exchange material; and
(c) eluting the retained peptide from the cation exchange material with an alkaline or neutral solution, wherein the alkaline or neutral solution comprises a volatile organic solvent, water, and a volatile compound selected from a volatile base, a volatile salt and a combination thereof.

2. A method of purifying a biological sample, comprising:
(a) contacting the biological sample with a hydrophobic, polymer-based cation exchange material under acidic conditions, such that the sample binds to the cation exchange material, wherein the sample comprises:
(i) a peptide,
(ii) a monovalent cationic contaminant and/or a hydrophobic contaminant, and
(iii) a hydrophilic contaminant;
(b) washing the cation exchange material with a first acidic solution, wherein the first acidic solution comprises greater than 20% (v/v) volatile organic solvent, water, and a volatile salt, such that the peptide is retained on the cation exchange material and the monovalent cationic and/or hydrophobic contaminant is removed from the cation exchange material;
(c) washing the cation exchange material with a second acidic solution, wherein the second acidic solution comprises 20% or less (v/v) volatile organic solvent, water, and a volatile acid, wherein the peptide is retained on the cation exchange material and the hydrophilic contaminant is removed; and
(d) eluting the retained peptide from the cation exchange material with an alkaline or neutral solution, wherein the alkaline or neutral solution comprises a volatile organic solvent, water, and a volatile compound selected from a volatile base, a volatile salt and a combination thereof.

3. A method of purifying a biological sample, comprising:
(a) contacting the biological sample with a hydrophobic, polymer-based cation exchange material under acidic conditions, such that the sample binds to the cation exchange material, wherein the biological sample comprises:
(i) a peptide,
(ii) a monovalent cationic contaminant and/or a hydrophobic contaminant, and
(iii) a hydrophilic contaminant;
(b) washing the cation exchange material with a first acidic solution, wherein the first acidic solution comprises 20% or less (v/v) volatile organic solvent, water, and a volatile acid, such that peptide is retained on the cation exchange material and the hydrophilic contaminant is removed from the cation exchange material;
(c) washing the cation exchange material with a second acidic solution, wherein the second acidic solution comprises greater than 20% (v/v) volatile organic solvent, water and a volatile salt, wherein the peptide is retained on the cation exchange material and the monovalent cationic and/or hydrophobic contaminant is removed from the cation exchange material; and
(d) eluting the retained peptide from the cation exchange material with an alkaline or neutral solution, wherein the alkaline or neutral solution comprises a volatile organic solvent, water, and a volatile compound selected from a volatile base, a volatile salt, and a combination thereof.

4. The method of any one of the preceding clauses, wherein the hydrophilic contaminant is a neutral contaminant, an anionic contaminant, or a combination thereof.

5. The method of any one of the preceding clauses, wherein the biological sample further comprises a salt, detergent, a lipid, a small neutral molecule, or a combination thereof.

6. The method of any one of the preceding clauses, comprising contacting the sample with the hydrophobic, polymer-based cation exchange material at a pH 1-5.

7. The method of any one of the preceding clauses, comprising washing the cation exchange material at a pH 1-5.

8. The method of any one of the preceding clauses, comprising eluting the sample from the cation exchange material at greater than pH 5 (e.g, 5-11).

9. The method of any one of the preceding clauses, wherein the monovalent cationic contaminant is selected from the group consisting of ammonium, sodium, potassium, tris(hydroxymethyl)aminomethane (tris), hydroxylamine, ethanolamine, HEPES (4-(2-hydroxyethyl)-1-piperazineethanesulfonic acid), PIPES (piperazine-N,N'-bis(2-ethanesulfonic acid)), EPPS (4-(2-Hydroxyethyl)-1-piperazinepropanesulfonic acid), glycine, a mass tag, and a combination thereof.

10. The method of any one of the preceding clauses, wherein the monovalent cationic contaminant is or comprises a mass tag or derivative thereof.

11. The method of any one of the preceding clauses, wherein hydrophobic contaminant is a lipid or a detergent.

12. The method of any one of the preceding clauses, wherein the hydrophilic contaminant is a salt, nucleic acid, or a carbohydrate.

13. The method of any one of the preceding clauses, treating the biological sample with a proteolytic enzyme (e.g., trypsin or Lys-C) to produce the peptide prior to contacting the biological sample with the cation exchange material.

14. A kit for purifying a biological sample comprising a peptide, comprising:
(a) a hydrophobic, polymer-based cation exchange material;
(b) an acidic solution comprising a volatile salt, water and greater than 20% (v/v) volatile organic solvent;
(c) a neutral or alkaline solution comprising a volatile base, water and a volatile organic solvent; and
(d) instructions for using the kit to purify the biological sample.

15. A kit for purifying a biological sample comprising a peptide, comprising:
(a) a hydrophobic, polymer-based cation exchange material;

(b) an acidic solution comprising greater than 20% (v/v) volatile organic solvent, a volatile salt, and water, (c) an acidic solution comprising 20% or less (v/v) volatile organic solvent, a volatile salt, and water;

(d) a neutral or alkaline solution comprising a volatile base, water, and a volatile organic solvent; and (e) instructions for using the kit to purify the biological sample.

16. The method or kit of any one of the preceding clauses, wherein the hydrophobic, polymer-based cation exchange material is sulfonated divinyl benzene polystyrene, sulfonated polydivinyl benzene, or sulfonated divinyl benzene/polystyrene/pyrrolidone resin.

17. The method or kit of any one of the preceding clauses, wherein the peptide comprises 2-50 amino acid residues.

18. The method or kit of any one of the preceding clauses, wherein the volatile salt comprises a volatile acid and a volatile base.

19. The method or kit of any one of the preceding clauses, wherein the volatile acid is selected from the group consisting of formic acid, acetic acid, trifluoroacetic acid, trichloroacetic acid.

20. The method or kit of any one of the preceding clauses, wherein the volatile base is selected from the group consisting of trimethylamine, ammonia, triethylamine, piperidine, and butylamine.

21. The method or kit of any one of the preceding clauses, wherein the volatile organic solvent is selected from the group consisting of acetonitrile, methanol, ethanol, n-propanol, iso-propanol, acetone, and a combination thereof.

21. The method or kit of any one of the preceding clauses, wherein the sample comprises two or more peptides.

22. The method or kit of any one of the preceding clauses, wherein the sample is a digested protein or polypeptide.

23. The method of any one of the preceding clauses, comprising eluting the retained peptide from the cation exchange material with an alkaline or neutral solution, wherein the alkaline or neutral solution comprises a volatile organic solvent, water, and a volatile salt.

What is claimed is:

1. A method of purifying peptides from a biological sample, comprising:

(a) contacting the biological sample with a hydrophobic, polymer-based cation exchange material under acidic conditions, such that the biological sample binds to the cation exchange material, wherein the biological sample comprises:

(i) at least one peptide, (ii) at least one monovalent cationic contaminant and/or a at least one hydrophobic contaminant, and (iii) at least one hydrophilic contaminant;

(b) washing the cation exchange material with a first volatile acidic solution, wherein the first volatile acidic solution comprises 20% or less (v/v) volatile organic solvent, water, and a first volatile acid, such that the at least one peptide is retained on the cation exchange material and the at least one hydrophilic contaminant is removed from the cation exchange material;

(c) washing the cation exchange material with a first volatile salt solution comprising a second volatile acidic solution, and a first volatile base solution, wherein the second volatile acidic solution comprises greater than 20% (v/v) volatile organic solvent, and water, such that the at least one peptide is retained on the cation exchange material and the at least one monovalent cationic and/or the at least one hydrophobic contaminant is removed from the cation exchange material; and (d) eluting the retained peptide from the cation exchange material with a volatile alkaline or neutral solution, wherein the volatile alkaline or neutral solution comprises a volatile organic solvent, water, and a volatile compound selected from a first or a second volatile base, a first or a second volatile salt, and a combination thereof.

2. The method of claim 1, wherein the hydrophilic contaminant is a neutral contaminant, an anionic contaminant, or a combination thereof.

3. The method of claim 1, wherein the biological sample further comprises a salt, detergent, a lipid, a small neutral molecule, or a combination thereof.

4. The method of claim 1, comprising contacting the sample with the hydrophobic, polymer-based cation exchange material at a pH 1-5.

5. The method of claim 1, comprising washing the cation exchange material at a pH 1-5.

6. The method of claim 1, comprising eluting the sample from the cation exchange material at greater than pH 5.

7. The method of claim 1, wherein the monovalent cationic contaminant is selected from the group consisting of ammonium, sodium, potassium, tris(hydroxymethyl)aminomethane (tris), hydroxylamine, ethanolamine, HEPES (4-(2-hydroxyethyl)-1-piperazineethane sulfonic acid), PIPES (piperazine-N,N'-bis(2-ethanesulfonic acid)), EPPS (4-(2-Hydroxyethyl)-1-piperazinepropanesulfonic acid), glycine, a mass tag, and a combination thereof.

8. The method of claim 1, wherein the monovalent cationic contaminant is or comprises a mass tag or derivative thereof.

9. The method of claim 1, wherein hydrophobic contaminant is a lipid or a detergent.

10. The method of claim 1, wherein the hydrophilic contaminant is a salt, nucleic acid, or a carbohydrate.

11. The method of claim 1, further comprising treating the biological sample with a proteolytic enzyme to produce the peptide prior to contacting the biological sample with the cation exchange material.

12. The method of claim 1, wherein the hydrophobic, polymer-based cation exchange material is sulfonated divinyl benzene polystyrene, sulfonated polydivinyl benzene, or sulfonated divinyl benzene/polystyrene/pyrrolidone resin.

13. The method of claim 1, wherein the first and/or second volatile acid is selected from the group consisting of formic acid, acetic acid, trifluoracetic acid, trichloroacetic acid.

14. The method of claim 1, wherein the first and/or second volatile base is selected from the group consisting of trimethylamine, ammonia, triethylamine, piperidine, and butylamine.

15. The method of claim 1, wherein the volatile organic solvent is selected from the group consisting of acetonitrile, methanol, ethanol, n-propanol, iso-propanol, acetone, and a combination thereof.

16. The method of claim 1, wherein the sample comprises two or more peptides, a digested protein, or a polypeptide, a labeled peptide, a labeled peptide digest, a mass tag labeled peptide, a mass tag labeled peptide digest, a tandem mass tag (TMT)-labeled peptide, or a tandem mass tag (TMT)-labeled peptide digest.

17. The method of claim 11, wherein the proteolytic enzyme is trypsin, Lys-C, AspN, or GluC.

18. The method of claim 1, wherein the first and/or second volatile salt is selected from ammonium acetate, ammonium formate, ammonium trifloroacetate, triethylammonium formate, triethylammonium acetate, triethylammonium trifluo-
roacetate and ammonium bicarbonate.

* * * * *